(12) United States Patent
Fujii et al.

(10) Patent No.: US 6,800,611 B2
(45) Date of Patent: Oct. 5, 2004

(54) METASTIN DERIVATIVES AND THEIR USE

(75) Inventors: Nobutaka Fujii, Otsu (JP); Ryuichiro Doi, Kyoto (JP); Shinya Oishi, Kyoto (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/337,105

(22) Filed: Jan. 6, 2003

(65) Prior Publication Data

US 2004/0142875 A1 Jul. 22, 2004

(51) Int. Cl.[7] .................. A61K 38/07; A61K 38/08; C07K 5/10; C07K 7/06

(52) U.S. Cl. .................. 514/17; 514/18; 530/329; 530/330

(58) Field of Search .................. 530/329, 330, 530/345; 514/17, 18

(56) References Cited

FOREIGN PATENT DOCUMENTS

| WO | WO 00/24890 | 5/2000 |
|----|-------------|--------|
| WO | WO 01/75104 | 10/2001 |
| WO | WO 02/85399 | 10/2002 |

OTHER PUBLICATIONS van Staveren et al. Labelling of [Leu5]–enkephalin with organometallic Mo complexes by solid–phase synthesis. Chemical Communications. 2002. pp. 1406–1407.*

Lee, JH et al., *KiSS–1, a Novel Human Malignant Melanoma Metastasis–Suppressor Gene* Journal of the National Cancer Institute, vol. 88, No. 23, Dec. 4, 1996, pp. 1731–1737.

Lee, JH et al., *Sappression of Metastasis in Human Brease Carcinoma MDA–MB–435 Cells after Transfection with the Metastasis Suppressor Gene, KiSS–1*, Cancer Research 57, Jun. 15, 1997, pp. 2384–2387.

Yan, C. et al., *KiSS–1 Represesses 92kDa Type IV Collagenase Expression by Down–regulating NF–kB Binding to the Promoter as a Consequence of IkBa–induced Block of p65/p50 Nuclear Translocation* Journal of Biological Chemistry vol. 276, Issue of Jan. 12, 2001 pp. 1164–1172.

Muir, Ai et al., *AXOR12, a Novel Human G Protein–coupled Receptor, Activated by the Peptide KiSs–1*, Journal of Biological Chemistry, vol. 276, No. 31, Issue of Aug. 2, 2001, pp. 28969–28975.

Ohtaki, T. et al. *Metastasis suppressor gene KiSS–1 encodes peptide ligand of a G–protein–coupled receptor*, Nature, vol. 411, May 31, 2001, pp. 613–617.

Hori, A. et al., *Metastin Suppresses the Motility and Growth of CHO Cells Transfected with its Receptor* Biochemical Biophysical Research Communications, vol. 286, 2001, pp. 958–963.

Kotani, M. et al., *The Metastasis Suppressor Gene KiSS–1 Encodes Kisspeptins, the Natural Ligands of the Orphan G Protein–coupled receptor GPR54*, Journal or Biological Chemistry, vol. 276, No. 37, Issue of Sep. 14, 2001, pp. 34631–34636.

(List continued on next page.)

*Primary Examiner*—Jeffrey Edwin Russel
(74) *Attorney, Agent, or Firm*—David G. Conlin; Jun Umemuro; Edwards & Angell, LLP

(57) ABSTRACT

The invention relates to metastin derivatives represented by the formula: X-AA$_1$-AA$_2$-AA$_3$-AA$_4$-Z (I), or a salt thereof, or a pro-drug thereof, which have cancer metastatis suppressing activity and cancer proliferation suppressing activity. The invention also relates to the use of these derivatives as drugs for preventing or treating cancers.

10 Claims, 10 Drawing Sheets p=0.0183

OTHER PUBLICATIONS

Lee, DK. Et al., *Discovery of a receptor related to the galanin receptors* Federation of European Biochemical Societies Letters. vol. 446, 1999, pp. 103–107.

West, A. et al., *Chomosome Localization and Genomic Structure of the KiSS–1 Metastasis Suppressor Gene (KiSS1)*, Genomics, vol. 54, 1998, pp. 145–148.

Rigaud, G. et al., *Allelotype of Pancreatic Acinar Cell Carcinoma*, Int. J Cancer, vol. 88, 2000, , pp. 772–777.

Yatsuoka, T. et al., *Association of Poor Prognosis With Loss of 12q, 17p, and 18q, and Concordant Loss of 6q/ 17p and 12q/ 18q in Human Pancreatic Ductal Adenocarcinoma*, The American Journal of Gastroenterology, vol. 95, No. 8, 2000, pp. 2080–2085.

Harada, T. et al., *Detection of Genetic Alterations in Pancreatic Cancers by Comparative Genomic Hybridization Coupled with Tissue Microdissection and Degenerate Oligonucleotide Primed Polymerase Chain Reaction*, Oncology vol. 62, 2002, pp. 251–258.

\* cited by examiner

Figure 6

KiSS-1

MNSLVSWQLLLFLCATHFGEPLEKVASVGNSRPTGQQLESLGLLAP
GEQSLPCTERKPAATARLSRRGTSLSPPPESSGSRQQPGLSAPHSR
QIPAPQGAVLVQREKDLPNYNWNSFGLRFGKREAAPGNHGRSAGR
GWGAGAGQ metastin

GTSLPPPESSGSRQQPGLSAPHSRQIPAPQGAVLVQREKDLPNYNW
NSFGLRF-NH$_2$

FMO53a

Gu-Amb-Phe-Gly-Leu-Arg-Trp-NH$_2$

FMO52a

Bis(Py)-Amb-Phe-Gly-Leu-Arg-Trp-NH$_2$

SEQUENCE LISTING

<160> NUMBER OF SEQ ID NOS: 10

<210> SEQ ID NO 1
<211> LENGTH: 53
<212> TYPE: PRT
<213> ORGANISM: Homo sapiens

```
<220> FEATURE:
<223> OTHER INFORMATION: C-term amidated

<400> SEQUENCE: 1

Gly Thr Ser Leu Pro Pro Glu Ser Gly Ser Arg Gln Gln Pro
 1               5                  10                  15

Gly Leu Ser Ala Pro His Ser Arg Gln Ile Pro Ala Pro Gln Gly Ala
                 20                  25                  30

Val Leu Val Gln Arg Glu Lys Asp Leu Pro Asn Tyr Asn Trp Asn Ser
         35                  40                  45

Phe Gly Leu Arg Phe
         50

<210> SEQ ID NO 2
<211> LENGTH: 145
<212> TYPE: PRT
<213> ORGANISM: Homo sapiens

<400> SEQUENCE: 2

Met Asn Ser Leu Val Ser Trp Gln Leu Leu Phe Leu Cys Ala Thr
 1               5                  10                  15

His Phe Gly Glu Pro Leu Glu Lys Val Ala Ser Val Gly Asn Ser Arg
                 20                  25                  30

Pro Thr Gly Gln Gln Leu Glu Ser Leu Gly Leu Ala Pro Gly Glu
         35                  40                  45

Gln Ser Leu Pro Cys Thr Glu Arg Lys Pro Ala Ala Thr Ala Arg Leu
     50                  55                  60

Ser Arg Arg Gly Thr Ser Leu Ser Pro Pro Glu Ser Ser Gly Ser
 65                  70                  75                  80

Arg Gln Gln Pro Gly Leu Ser Ala Pro His Ser Arg Gln Ile Pro Ala
                 85                  90                  95

Pro Gln Gly Ala Val Leu Val Gln Arg Glu Lys Asp Leu Pro Asn Tyr
                100                 105                 110

Asn Trp Asn Ser Phe Gly Leu Arg Phe Gly Lys Arg Glu Ala Ala Pro
            115                 120                 125

Gly Asn His Gly Arg Ser Ala Gly Arg Gly Trp Gly Ala Gly Ala Gly
        130                 135                 140

Gln
        145

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide FMO53a
<220> FEATURE:
<223> OTHER INFORMATION: C-term amidated

<400> SEQUENCE: 3

Phe Gly Leu Arg Trp
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide FMO52a
```

<220> FEATURE:
<223> OTHER INFORMATION: C-term amidated

<400> SEQUENCE: 4

Phe Gly Leu Arg Trp
 1               5

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
actcactggt tcttggcag c                                       21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
accttttcta atggctcccc a                                      21

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Probe

<400> SEQUENCE: 7
actgctttcc tctgtgccac ccact                                  25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
cgacttcatg tgcaagttcg tc                                     22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
cacactcatg gcggtcagag                                        20

<210> SEQ ID NO 10
<211> LENGTH: 27
<212> TYPE: DNA
<213> ORGANISM: Artificial Sequence

```
<220> FEATURE:
<223> OTHER INFORMATION: Description of Artificial Sequence: Probe

<400> SEQUENCE: 10
actacatcca gcaggtctcg gtgcagg                                              27
```

METASTIN DERIVATIVES AND THEIR USE

TECHNICAL FIELD

The present invention relates to novel metastin derivatives and their use.

BACKGROUND OF THE INVENTION

It is well known that cancer is one of the leading causes of death throughout the world. Recent strategies for treating cancer have focussed on metastasis. In this process, cancer cells dissociate from malignant tumors and then invade surrounding or distant tissue, where they proliferate. It has been found that the product from the gene known as KiSS-1 suppresses metastasis of human melanomas and breast carcinomas.

The KiSS1 peptide was originally identified as being differentially up-regulated in C8161 melanoma cells that have been rendered nonmetastatic by microcell-mediated transfer of human chromosomes. (Lee, J H et al., *J Natl Cancer Inst* 1996, 88, 1731-7). It has been found that transfection of KiSS1 into human melanoma and breast carcinoma cells prevents these cells from metastasizing without cellular proliferation. (Lee, J H et al., *Cancer Res* 1997, 57, 2384–72). Furthermore, the KISS1 gene product has been shown to repress 92-kDa type4 collagenase (MMP-9) expression by effecting reduced NF-kB binding to the promoter. (Yan, C. et al., *J Biol Chem* 2001, 276, 1164–72). The KISS1 gene product was found to be expressed in normal human placenta, testis, brain, pancreas and liver. (Muir, A I et al., *J Biol Chem* 2001, 276, 28969-75).

KiSS-1 encodes a 145-amino acid residue peptide, which is further processed to a final 54-amino acid peptide with C-terminal amidation. The 54 amino acid peptide called "metastin" is the ligand to a G-protein-coupled orphan receptor known as OT7T175 or AXOR12. (Muir, A I. et al., supra; Ohtaki, T, et al., *Nature* 2001, 411, 613–7; Hori, A. et al., *Biochem Biophys Res Commun* 2001, 286, 958–63; Kotani, M. et al., *J Biol Chem* 2001, 276, 34631–6). This receptor has a high degree of homology to the rat orphan heptahelical receptor GPR54 (Lee, D K. et al., *FEBS Lett* 1999, 446, 103–7), (81% amino acid identity), which suggest that these two receptors are orthologs. Metastin enhanced the expression and activity of focal adhesion kinase, and attenuates pulmonary metastasis of hOT7T175 transfected B16-BL6 melanomas in vivo. (Ohtaki, T. et al., supra.) Metastin was also found to inhibit chemotaxis and invasion of hOT7T175 transfected Chinese hamster ovary (CHO) cells in vitro with activation of phospholipase C, arachidonic acid relase, and phosphorylation of ERK. (Hori, A. et al., supra and Kotani, M. et al., supra.) Although these pathways typically induce cellular proliferation, change in cell growth was not observed.

The KiSS1 gene is located on human chromosome1q32–q41. (West, A. et al., *Genomics* 1998, 54, 145–8). However, evidence from subsequent experiments suggests that the expression of KiSS1 is very likely to be regulated by a gene or genes located in the 40-cM region between 6q16.3–q23. (Lee, J H. et al., *J Natl Cancer Inst* 1996, 88, 1731–7). In pancreatic cancer, losses of 6q, 8p, 9p, 17p, and 18q were frequently observed and those alterations tend to cause lymph node metastasis and distant metastasis, which suggests the existence of a metastasis suppressor gene or genes responsible for pancreatic carcinoma metastasis on these regions. (Rigaud, G, et al., *Int J Cancer* 2000, 88, 772–7 ; Yatsuoka, T. et al., *Am J Gastroenterol* 2000, 95, 2080–5; Harada, T. et al., *Oncology* 2002, 62, 251–8). These suggest that pancreatic cancer is associated with down regulation of metastin expression. Moreover, in other cancers such as ovarian and breast carcinoma as well as thyroid papillary cancer, overexpression of the metastin receptor, hOT7T175, has been demonstrated, as compared to normal tissue (Muir, A I. et al, supra; Ohtaki, T. et al., supra), although metastin itself is less frequently overexpressed in the tumor tissue. (Lee, J H.et al, supra). The expression of KiSS-1, i.e., metastin production, and the expression of its receptor in pancreatic cancer has not yet been studied. Similarly, the effects of metastin on the movement of cancer cells that endogenously express the receptor have not been investigated.

These findings indicate that KISS1-hOT7T175 acts as a metastasis suppressor system. Because metastin inhibits metastasis of cancer cells without affecting cellular growth properties in normal cells, it is desirable to target the metastin receptors for cancer therapy. Thus, it would be desirable to have compounds that bind metastin receptors, suppress cancer metastasis and/or suppress cancer proliferation. Furthermore, it would be useful to have compounds that have metastasis suppressing activity and that can be used to treat acute or chronic pancreatitis or pancreatic cancer.

WO00/24890 discloses human metastin, WO01/75104 discloses mouse or rat metastin and WO02/85399 discloses a sustained release preparation comprising metastin. These references disclose that metastin can suppress cancer metastasis. However, it is desirable to develop compounds that suppress cancer metastasis and cancer proliferation and that are useful as therapeutic agents for the treatment of cancers.

SUMMARY OF THE INVENTION

The present inventors found that by making certain modifications to peptides corresponding to, or analogous to, a portion of the metastin amino acid sequence, the resulting derivatives are stable and exhibit outstanding cancer metastasis inhibiting activity and cancer proliferation inhibiting activity.

The present invention provides a metastin derivative represented by the formula:

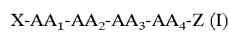

wherein X is a group represented by the formula:

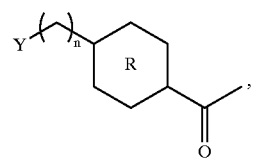

wherein Y is a group represented by the formula:

(i)

(ii)

$$\begin{array}{c} R^1 \\ | \\ R^2\text{-N} \\ \diagdown \\ R^3\text{-N} \end{array}$$

(iii)

$$R^1, R^2, R^3, R^4 \text{ structure}$$

(iv)

$$\text{pyrimidine with } R^1, R^2, R^3$$

(v)

$$W^1\text{-CH}_2\text{-N-CH}_2\text{-W}^2$$

wherein $R^1$, $R^2$, $R^3$ and $R^4$ are each selected from a hydrogen atom or a $C_{1-6}$ alkyl group;

$W^1$ and $W^2$ are each selected from a hydrogen atom, a $C_{1-6}$ alkyl group, a $C_{6-14}$ aryl group or a heterocyclic group;

R is represented by the formula:

(cyclohexyl-1,4-diyl) or (phenyl-1,4-diyl);

n is 0,1 or 2;

$AA_1$ is a natural or unnatural aromatic amino acid;

$AA_2$ is Gly, Ala, Pro or Pic;

$AA_3$ is an aliphatic amino acid;

$AA_4$ is a basic amino acid or citrulline;

Z is selected from:
(i) a natural or unnatural aromatic amino acid, or an amide thereof, or an ester thereof,
(ii) a group represented by the formula:

(Wa) indole structure wherein $n_1$ is 0, 1 or 2

(iii) a group represented by the formula:

(Wb) naphthalene structure wherein $n_2$ is 0, 1 or 2, or
(iv) a group represented by the formula:

(Wc) phenyl structure wherein $n_2$ is 0,1 or 2, or a salt thereof;

The present invention also provides a metastin derivative (I) as defined above, which is 4-[N,N-Bis(2-pyridylmethyl) aminomethyl]benzoyl-Phe-Gly-Leu-Arg-Trp-NH$_2$ (FM052a) (SEQ ID NO: 4), 4-(guanidinomethyl)benzoyl-Phe-Gly-Leu-Arg-Trp-NH$_2$ (FM053) (SEQ ID NO: 3) or a salt thereof.

The present invention also provides a pro-drug of a metastin derivative (I) as defined above or a salt thereof.

The present invention also provides pharmaceutical compositions comprising a metastin derivative (I) as defined above, or a salt thereof or a pro-drug thereof. The pharmaceutical compositions of the present invention are useful an agents for suppressing cancer metastasis or a agents for suppressing cancer proliferation. The pharmaceutical compositions of the present invention are also useful agents for preventing or treating cancer.

The pharmaceutical compositions of the present invention are also useful agents for regulating a function of the pancreas. The pharmaceutical compositions of the present invention are especially useful agents for preventing or treating acute or chronic pancreatitis or pancreatic cancer.

The present invention also provides pharmaceutical compositions comprising a metastin derivative (I) as defined above, or a salt thereof or a pro-drug thereof, which are useful agents for regulating functions of the placenta.

The present invention also provides phannaceutical compositions comprising a metastin derivative (I) as defined above, or a salt thereof or a pro-drug thereof, which are useful agents for preventing or treating cilia cancer, hydatid moles, invasive moles, miscarriage, fetal hypoplasia, sugar dysbolism, lipid dysbolism or labor induction.

The present invention also provides a method for suppressing cancer metastasis or suppressing cancer proliferation in a mammal which comprises administering to the mammal an effective amount of a metastin derivative (I) as defined above, or a salt thereof or a pro-drug thereof.

The present invention also provides a method for preventing or treating cancer in a mammal which comprises administering to the mammal an effective amount of a metastin derivative (I) as defined above, or a salt thereof or a pro-drug thereof.

The present invention also provides a method for regulating a function of the pancreas of a mammal, which comprises administering to a mammal an effective amount of a metastin derivative (I) as defined above, or a salt thereof or a pro-drug thereof.

The present invention also provides a method for preventing or treating acute or chronic pancreatitis or pancreatic cancer in a mammal, which comprises administering to a mammal an effective amount of a metastin derivative (I) as defined above, or a salt thereof or a pro-drug thereof.

The present invention also provides a method for regulating a function of a placenta of a mammal which comprises administering to the mammal an effective amount of a metastin derivative (I) as defined above, or a salt thereof or a pro-drug thereof.

The present invention also provides a method for preventing or treating cilia cancer, hydatid mole, invasive mole, miscarriage, fetal hypoplasia, sugar dysbolism, lipid dysbolism or labor induction in a mammal which comprises administering to the mammal an effective amount of a metastin derivative (I) as defined above, or a salt thereof or a pro-drug thereof.

The present invention also provides an agent for suppressing cancer metastasis or an agent for suppressing cancer proliferation comprising a metastin derivative (I) as defined above, or a salt thereof or a pro-drug thereof.

The present invention also provides an agent for preventing or treating cancer comprising a metastin derivative (I) as defined above, or a salt thereof or a pro-drug thereof.

The present invention also provides an agent for regulating a function of the pancreas of a mammal comprising a metastin derivative (I) as defined above, or a salt thereof or a pro-drug thereof.

The present invention also provides an agent for preventing or treating acute or chronic pancreatitis or pancreas cancer comprising a metastin derivative (I) as defined above, or a salt thereof or a pro-drug thereof.

The present invention also provides an agent for regulating a function of placenta comprising a metastin derivative (I) as defined above, or a salt thereof or a pro-drug thereof.

The present invention also provides an agent for preventing or treating cilia cancer, hydatid mole, invasive mole, miscarriage, fetal hypoplasia, sugar dysbolism, lipid dysbolism or labor induction comprising a metastin derivative (I) as defined above, or a salt thereof or a pro-drug thereof.

BRIEF DESCRIPTION OF THE DRAWINGS

FIG. 6 shows peptide sequence of KiSS-1 peptide (SEQ ID NO: 2) and its derivatives (SEQ ID NOS 1, 3 & 4, respectively, in order of appearance).

DETAILED DESCRIPTION OF THE INVENTION

Figure 1:
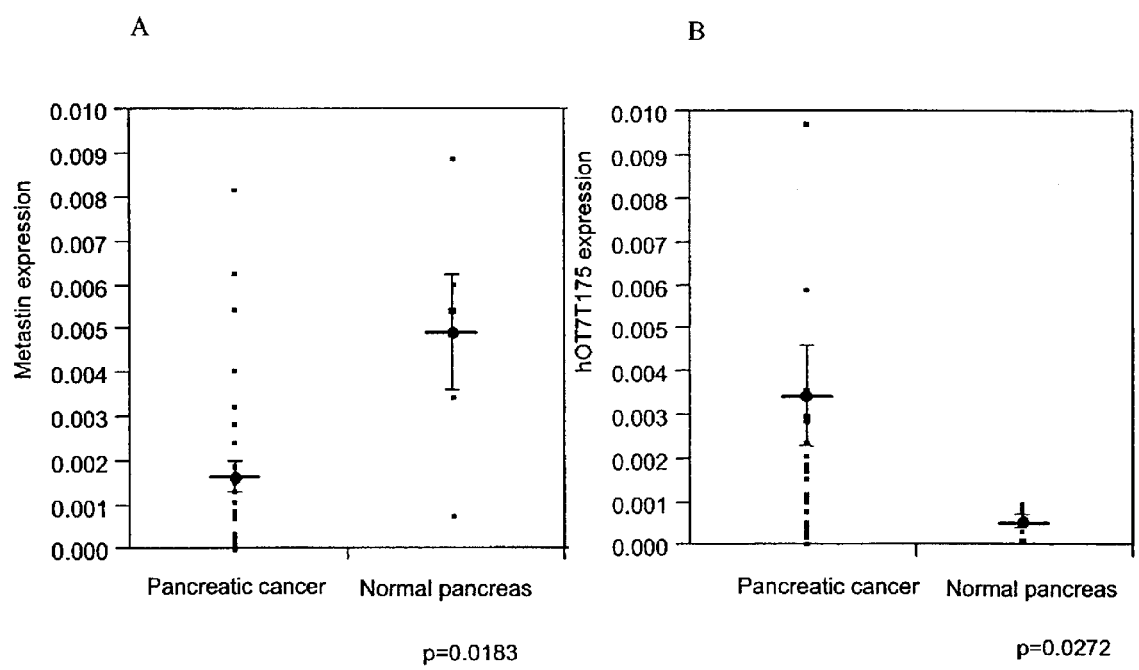
FIG. 1A shows expression of Metastin mRNA in pancreatic cancer tissues.
FIG. 1B shows expression of hOT7T175 mRNA in pancreatic cancer tissues.

In the formulae, X is a group represented by the formula:

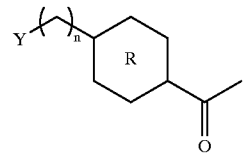

wherein each symbol has the same meaning as defined above.

Y is a group represented by the following formulae: (i)

(i)

(Y$^1$)

(ii)

(Y$^2$)

(iii)

(Y$^3$)

(iv)

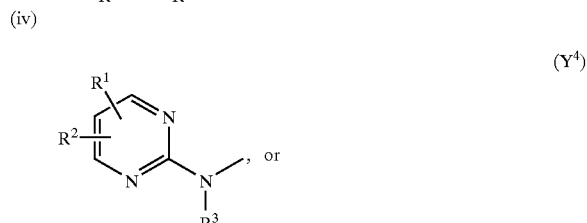
(Y$^4$)

, or (v)

(Y$^5$)

wherein R$^1$ to R$^4$ are each selected from a hydrogen atom or a C$_{1-6}$ alkyl group, and W$^1$ and W$^2$ are each selected from a hydrogen atom, a C$_{1-6}$ alkyl group, a C$_{6-14}$ aryl group or a heterocyclic group.

The C$_{1-6}$ alkyl group includes methyl, ethyl, propyl, isopropyl, butyl, isobutyl, sec-butyl, tert-butyl, pentyl, isopentyl, neopentyl, hexyl, etc. In certain embodiments a $C_{1-3}$ alkyl group such as methyl, ethyl is preferred.

In embodiments where Y is $Y^3$, $R^1$ to $R^4$ are each preferably a hydrogen atom.

The $C_{6-14}$ aryl group includes phenyl, 1-naphthyl, 2-naphthyl, 2-biphenylyl, 3-biphenylyl, 4-biphenylyl and 2-anthryl.

The heterocyclic group used for $W^1$ and $W^2$ includes a 5 to 14 membered (monocyclic, bicyclic or tricyclic) heterocyclic group containing 1 to 4 hetero atoms selected from a nitrogen atom, a sulfur atom and an oxygen atom in addition to carbon atoms. Preferably (i) a 5 to 14 membered (preferably 5 to 10 membered) aromatic heterocyclic group, (ii) a 5 to 10 membered non-aromatic heterocyclic group or (iii) a monovalent group obtained by removing one arbitrary hydrogen atom from a 7 to 10 membered heterocyclic bridge ring, etc. and a 6 membered aromatic heterocyclic group is used. Specific examples of the heterocyclic groups include, but are not limited to, an aromatic heterocyclic group such as thienyl (2-thienyl, 3-thienyl), furyl (2-furyl, 3-furyl), pyridyl (2-pyridyl, 3-pyridyl, 4-pyridyl), thiazolyl (2-thiazolyl, 4-thiazolyl, 5-thiazolyl), oxazolyl (2-oxazolyl, 4-oxazolyl), quinolyl (2-quinolyl, 3-quinolyl, 4-quinolyl, 5-quinolyl, 8-quinolyl), isoquinolyl (1-isoquinolyl, 3-isoquinolyl, 4-isoquinolyl, 5-isoquinolyl), pirazinyl, pyrimidinyl (2-pyrimidinyl, 4-pyrimidinyl), pyrrolyl (1-pyrrolyl, 2-pyrrolyl, 3-pyrrolyl), imidazolyl (1-imidazolyl, 2-imidazolyl, 4-imidazolyl), pyrazolyl (1-pyrazolyl, 3-pyrazolyl, 4-pyrazolyl), pyridazinyl (3-pyridazinyl, 4-pyridazinyl), isothiazolyl (3-isothiazolyl), isooxazolyl (3-isooxazolyl), indolyl (1-indolyl, 2-indolyl, 3-indolyl), 2-benzothiazolyl, benzo[b]thienyl (2-benzo[b]thienyl, 3-benzo[b]thienyl), benzo[b]furanyl (2-benzo[b]furanyl, 3-benzo[b]furanyl) and the like, and a non-aromatic heterocyclic group such as pyrrolidinyl (1-pyrrolidinyl, 2-pyrrolidinyl, 3-pyrrolidinyl), oxazolidinyl (2-oxazolidinyl), imidazolinyl (1-imidazolinyl, 2-imidazolinyl, 4-imidazolinyl), piperidinyl (1-pyperidinyl, 2-piperidinyl, 3-piperidinyl, 4-piperidinyl), piperazinyl (1-piperazinyl, 2-piparazinyl), morpholino, thiomorpholino and the like.

Preferable examples of $W^1$ and $W^2$ include a 2-pyridyl group, 3-pyridyl group, 4-pyridyl group, etc.

In preferred embodiments, Y is selected from $Y^3$, $Y^5$, a N,N-bis-(2-pyridylmethyl)amino group and a 4-guanidino group.

R is

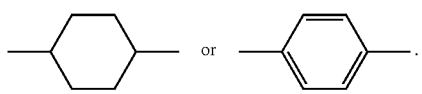

In certain embodiments, R is preferably

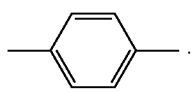

In the compounds of the invention, n is 0, 1 or 2. In certain embodiments, n=1 is more preferred.

Preferable examples of X are 4-(N,N-bis-(2-pyridylmethyl) aminomethyl)benzoyl or 4-(guanidinomethyl)benzoyl.

$AA_1$ is a natural or unnatural aromatic amino acid. Examples of useful aromatic amino acids include Phe, Trp, Tyr, His or 1- or 2-naphthylalanine. In certain embodiments, $AA_1$ is preferably Phe.

$AA_2$ is selected from the group consisting of Gly, Ala, Pro or Pic. Preferable examples of $AA_2$ are Gly, D-Ala, D-Pro or D-Pic. In certain embodiments, $AA_2$ is preferably Gly.

$AA_3$ is an aliphatic amino acid. Examples of useful aliphatic amino acids include Leu, Ile, Val, Nle, Ala and Met. In certain embodiments, $AA_3$ is preferably Leu.

$AA_4$ is a basic amino acid or citrulline. Examples of useful basic amino acids are Arg, Lys or Orn. In certain embodiments, $AA_4$ is preferably Arg.

Z is selected from:
(i) a natural or unnatural aromatic amino acid, or an amide thereof, or an ester thereof,
(ii) a group represented by the formula:

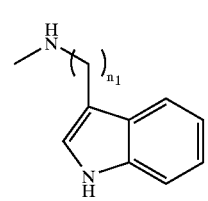

(Wa)

wherein $n_1$ is 0, 1 or 2,
(iii) a group represented by the formula:

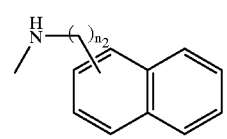

(Wb)

wherein $n_2$ is 0, 1 or 2, or
(iv) a group represented by the formula:

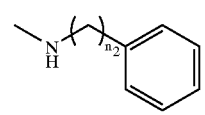

(Wc)

wherein $n_2$ is 0,1 or 2, or a salt thereof.

Examples of the aromatic amino acids useful for Z include the amides of Phe, Trp, Tyr, His or 1- or 2-naphthylalanine. In certain embodiments, Z is preferably the amide of Trp.

Preferable examples of the metastin derivative (I) of the present invention are compounds produced in the following preparation examples. The most preferable metastin derivatives of the present invention include FM052a and FM053a.

The metastin derivatives (I) of the present invention can be prepared by methods of synthesizing peptides known in the art. The method of synthesizing peptides may be, for example, by either of a solid phase synthesizing method or a solution phase synthesizing method. That is, an end peptide can he prepared by condensing a partial peptide or an amino acid which can constitute the peptide of the present invention and the remaining part and, when the product has a protecting group, eliminating the protecting group. Examples of known condensing methods and methods of eliminating a protecting group include the methods described in the following (1) to (5), which are incorporated herein in their entirety:

(1) M. Bodanszky and M. A. Ondetti, Peptide Synthesis, Interscience Publishers, New York (1966);
(2) Schroeder and Luebke, The Peptide, Academic Press, New York (1965);

(3) Nobuo Izumiya et al., Fundament and Experiment of Peptide Synthesis, Maruzen (K. K.) (1975);
(4) Haruaki Yazima and Syunpei Sakakibara, Biochemistry Experimental Course 1, Protein Chemistry IV, 205, (1977); and
(5) Supervised by Haruaki Yazima, Development of Medicaments, second series, vol. 14, Peptide Synthesis, Hirokawa Shoten.

In addition, after the reaction, the peptide of the present invention can be purified and isolated by combining the normal purifying methods, for example, solvent extraction, distillation, column chromatography, liquid chromatography, and recrystallization. When the peptide obtained by the aforementioned method is a free peptide, it can be converted into a suitable salt by known methods and, conversely, when the peptide is obtained as a salt, it can be converted into a free peptide by known methods.

Regarding condensation of a protected amino acid or peptide, various activating reagents which can be employed for peptide synthesis can be used and, in particular trisphosphonium salts, tetramethyluronium salts, carbodiimides are suitable. Examples of trisphosphonium salts include benzotriazol-1-yloxytris(pyrrolidino)phosphonium hexafluorophosphate (PyBOP), bromotris(pyrrolidino) phosphonium hexafluorophosphate (PyBroP) and 7-azabenzotriazol-1-yloxytris(pyrrolidino)phosphonium hexafluorophosphate (PyAOP), examples of tetramethyluronium salts include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluronium tetrafluoroborate (TBTU), 2-(5-norbornene-2,3-dicarboxyimido)-1,1,3,3-tetramethyluronium tetrafluoroborate (TNTU) and O-(N-succimidyl)-1,1,3,3-tetramethyluronium tetrafluoroborate (TSTU), and examples of carbodiimides include DCC, N,N'-diisopropylcarbodiimide (DIPCDI) and N-ethyl-N'-(3-dimethylaminopropyl) carbodiimide hydrochloride (EDCI·HCl). For condensation, the addition of racemization inhibiting agents (e.g. HONB, HOBt, HOAt, HOOBt etc.) is preferable. A solvent used in condensation can be appropriately selected from solvents which are known to be employed in a peptide condensing reaction. For example, acid amides such as anhydrous or hydrous N,N-dimethylformamide, N,N-dimethylacetoamide and N-methylpyrrolidone, halogenated hydrocarbons such as methylene chloride and chloroform, alcohols such as trifluoroethanol and phenol, sulfoxides such as dimethyl sulfoxide, tertiary amines such as pyridine, ethers such as dioxane and tetrahydrofuran, nitriles such as acetonitrile and propionitrile, esters such as methyl acetate and ethyl acetate, or suitable mixtures thereof are used. The reaction temperature is appropriately selected from a range which is known to be used in a peptide linkage forming reaction, and is usually appropriately selected from a range of about –20° C. to 50° C. An activated amino acid derivative is usually used at 1.5 to 6-fold excessive amount. In the case of solid phase synthesis, when condensation is insufficient as a result using a ninhydrin reaction, sufficient condensation can be performed by repeating the condensing reaction without performing elimination of a protecting group. When sufficient condensation can not be obtained by repeating the reaction, an unreacted amino acid can be acylated using acetic anhydride or acetylimidazole, causing no influence on the later reaction.

Examples of protecting groups which can be used on an amino group of the raw materials include Z, Boc, tertiary pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, or others known in the art. Examples of protecting groups for a carboxyl group include, in addition to the aforementioned $C_{1-6}$alkyl group, $C_{3-8}$cycloalkyl group and $C_{7-14}$aralkyl group as R, allyl, 2-adamantyl, 4-nitrobenzyl, 4-methoxybenzyl, 4-chlorobenzyl, phenacyl group, benzyloxycarbonylhydrazide, tertiary butoxycarbonylhydrazide, tritylhydrazide, or others known in the art.

The hydroxyl group of serine and threonine can be protected, for example, by esterification or etherification. Examples of groups suitable for this esterification include groups derived from lower ($C_{2-4}$) alkanoyl group such as acetyl group, and aroyl group such as benzoyl group, or others known in the art. In addition, examples of a group suitable for etherification include benzyl group, tetrahydropyranyl group, tertiary butyl group and trityl group (Trt).

Examples of protecting groups for a phenolic hydroxyl group of tyrosine include Bzl, 2,6-dichlorobenzyl, 2-nitrobenzyl, Br-Z, tertiary butyl, or others known in the art.

Examples of protecting groups for imidazole of histidine include Tos, 4-methoxy-2,3,6-trimethylbenzenesulfonyl (Mtr), DNP, Bom, Bum, Boc, Trt, Fmoc, or others known in the art.

Examples of protecting groups for a guanidine group of arginine include Tos, Z, 4-methoxy-2,3,6-trimethylbenzenesulfonyl (Mtr), p-methoxybenzenesulfonyl (MBS), 2,2,5,7,8-pentamethylchroman-6-sulfonyl (Pmc), mesitylene-2-sulfonyl (Mts), 2,2,4,6,7-pentamethyldihydrobenzofuran-5-sulfonyl (Pbf), Boc, Z, $NO_2$, or others known in the art.

Examples of protecting groups for side chain amino group of lysine include Z, Cl-Z, trifluoroacetyl, Boc, Fmoc, Trt, Mtr, 4,4-dimethyl-2,6-dioxocyclohexylideneyl (Dde), or others known in the art.

Examples of protecting groups for indolyl of tryptophan include formyl (For), Z, Boc, Mts, Mtr, or others known in the art.

A protecting group for asparagine and glutamine include Trt, xanthyl (Xan), 4,4'-dimethoxybenzhydryl (Mbh) and 2,4,6-trimethoxybenzyl (Tmob), or others known in the art.

Examples of an activated raw material carboxyl group include corresponding acid anhydride, azide, and active esters (esters with alcohols (e.g. pentachlorophenol, 2,4,5-trichlorophenol, 2,4-dinitrophenol, cyanomethyl alcohol, paranitrophenol, HONB, N-hydroxysuccinimide, 1-hydroxybenzotriazole (HOBt), 1-hydroxyl-7-azabenzotriazole (HOAt))). Examples of an activated raw material amino group include corresponding phosphorous acid amide.

Examples of methods for removing (eliminating) a protecting group include catalytic reduction in a hydrogen stream in the presence of a catalyst such as Pd black or Pd carbon, acid treatment with anhydrous hydrogen fluoride, methanesulfonic acid, trifluoromethanesulfonic acid, trifluoroacetic acid, trimesylsilane bromide (TMSBr), trimethylsilyl trifluoromethanesulfonate, tetrafluoroboric acid, tris(trifluoro)boron, boron tribromide or a mixed solution thereof, base treatment with diisopropylethylamine, triethylamine, piperidine or piperazine, and reduction with sodium in liquid ammonia. An eliminating reaction by the aforementioned acid treatment is generally performed at a temperature of –20° C. to 40° C. and, in acid treatment, addition of a cation scavenger such as anisole, phenol, thioanisole, methacresol and paracresol, or dimethyl sulfide, 1,4-butanedithiol or 1,2-ethanedithiol is effective. In addition, a 2,4-dinitrophenyl group used as a protecting group for imidazole of histidine is removed by treatment with thiophenol, and a formyl group used as a protecting group for indole of tryptophan is removed by alkali treatment with dilute sodium hydroxide or dilute ammonia in addition to deprotection by acid treatment in the presence of the aforementioned 1,2-ethanedithiol or 1,4-butanedithiol.

Protecting groups to protect functional groups which are not involved in the reaction of the raw material can be readily selected from known protecting groups or other means. Similarly, the elimination of the protecting groups and activation of the functional groups, which participates in the reaction can be achieved by methods known in the art.

To obtain an amide of a peptide, the amide is solid phase-synthesized using an amide synthesizing resin, or an α-carboxyl group of a carboxyl-terminal amino acid is amidated, a peptide chain is extended on an amino group side to a desired chain length, and only a protecting group for a N-terminal a-amino group of the peptide chain is removed to prepare a peptide, and only a protecting group for a C-terminal carboxyl group is removed to prepare a peptide (or amino acid), and both peptides are condensed in the aforementioned mixed solvent. The details of the condensing reaction are the same as those described above. The protected peptide obtained by condensation is purified and all the protecting groups arc removed by the aforementioned method, whereby, the desired crude peptide can be obtained. This crude peptide can be purified by using the known various purifying means and the main fractions can be freeze-dried to obtain an amide of the desired peptide.

When the metastin derivative (I) of the present invention is present as a configurational isomer, a diastereomer, a conformer or the like, each can be isolated by the aforementioned separating and purifying means, if desired. In addition, when the compound of the present invention is racemic, it can be separated into a S isomer and a R isomer by the normal optical resolving means.

When the metastin derivative (I) of the present invention has a steric isomer, the present invention includes the case where this isomer is alone and the case where the isomers are present as a mixture.

In addition, the metastin derivative (I) of the present invention may be hydrated or non-hydrated.

The metastin derivative (I) of the present invention may be labeled with an isotope element (e.g. $^{3}H$, $^{14}C$, $^{35}S$) or the like.

In peptides described herein, the left end is the N-terminal (amino terminal) and the right end is the C-terminal (carboxyl terminal) according to the custom designating peptides. The C-terminal of the peptide may be amide (—$CONH_2$), carboxyl group (—COOH), carboxylate (—COO—), alkylamide (—CONRR) or ester (—COOR) and, in particular, amide (—$CONH_2$) is preferable. Examples of R of the ester or alkylamide group include $C_{1-6}$alkyl group such as methyl, ethyl, n-propyl, isopropyl and n-butyl, $C_{3-8}$cycloalkyl group such as cyclopentyl and cyclohexyl, $C_{6-12}$aryl group such as phenyl and α-naphthyl, phenyl-$C_{1-2}$alkyl such as benzyl, phenethyl and benzhydryl, and $C_{7-14}$aralkyl group such as α-naphthyl-$C_{1-2}$alkyl such as α-naphthylmethyl and, additionally, pivaloyloxymethyl group which is generally used as an oral ester.

Examples of a salt of the metastin derivative (I) of the present invention include a metal salt, a salt with ammonium, a salt with an organic base, a salt with inorganic acid, a salt with organic acid, a salt with basic or acidic amino acid and the like. Preferable examples of a metal salt include alkali metal salts such as sodium salt, potassium salt and the like; alkaline earth metal salts such as calcium salt, magnesium salt, barium salt and the like; aluminium salt and the like. Preferable examples of a salt with organic base include salts with trimethylamine, triethylamine, pyridine, picoline, 2,6-lutidine, ethanolamine, diethanolamine, triethanolaimne, cyclohexylamine, dicyclohexylamine, N,N'-dibenzylethylenediamine and the like. Preferable examples of a salt with inorganic acid include salts with hydrochloric acid, hydrobromic acid, nitric acid, sulfuric acid, phosphoric acid and the like. Preferable examples of a salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of a salt with basic amino acid include salts with arginine, lysine, ornithine and the like, and preferable examples of a salt with acidic amino acid include salts with aspartic, glutamic acid and the like.

Among them, pharmaceutically acceptable salts are preferable. For example, when a compound has an acidic functional group, inorganic salts such as alkali metal salts (e.g. sodium salt, potassium salt etc), alkaline earth metal salts (e.g. calcium salt, magnesium salt, barium salt etc.), ammonium salt and the like are preferable. When a compound has a basic functional group, salts with inorganic acids with hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like are preferable.

A pro-drug of the metastin derivative (I) or a salt thereof (hereinafter referred to as the metastin derivative (I) of the present invention) means a compound which is converted to the metastin derivative (I) of the present invention under physiological conditions or with a reaction due to an enzyme, a gastric acid, etc. in the living body. That is, a pro-drug of the present invention is a compound which is converted to the metastin derivative (I) of the present invention with oxidation, reduction, hydrolysis, etc. by, e.g., to an enzyme or gastric acid, etc.

Examples of the pro-drug of the metastin derivative (I) of the present invention include: (a) a compound wherein an amino groupjof the metastin derivative (I) of the present invention is substituted with acyl, alkyl, phosphoric acid, etc (e.g., a compound wherein an amino group of the metastin derivative (I) of the present invention is substituted with eicosanoyl, alanyl. pentylaminocarbonyl (5-methyl-2-oxo-1,3-dioxolene-4-yl) methoxycarbonyl, tetrahydrofuranyl, pyrrolidylmethyl, pivaloyloxymethyl, tert-butyl, etc); (b) a compound wherein a hydroxy group of the metastin derivative (I) of the present invention is substituted with acyl, alkyl, phosphoric acid, boric acid, etc. (e.g. a compound wherein an hydroxy group of the metastin derivative (I) of the present invention is substituted with acetyl, palmitoyl, propanoyl, pivaloyl, succinyl, fumaryl, alanyl, dimethylaminomethylcarbonyl, etc.); and (c) a compound wherein a carboxyl group of the metastin derivative (I) of the present invention is substituted with ester, amide, etc. (e.g., a compound wherein a carboxyl group of the metastin derivative (I) of the present invention is substituted with ethylester, phenylester, carboxymethylester, dimethylaminomethylester, pivaloyloxymethylester, etoxycarbonyloxyethylester, phthalidylester, (5-methyl-2- oxo-1,3-dioxolene-4-yl) methylester, cyclohexyloxy-carbonylethylester, methylamide, etc).

These pro-drugs can be produced by known methods from the metastin derivative (I) of the present invention.

The pro-drug of the metastin derivative (I) of the present invention may be a compound which is converted into the metastin derivative (I) of the present invention under the physiological conditions as described in "Pharmaceutical Research and Development", Vol. 7 (Drug Design), pages 163–198 published in 1990 by Hirokawa Publishing Co. (Tokyo, Japan).

The metastin derivatives (I) of the present invention or a salt thereof or a pro-drug thereof (hereinafter referred to as the compound of the present invention) possess a cancer metastasis suppressing activity or a cancer proliferation suppressing activity. Thus the metastin compounds of the present invention are useful for pharmaceutical compositions such as an agent for preventing or treating all cancers (e.g., lung cancer, gastric cancer, liver cancer, pancreas cancer, large intestine cancer, rectal cancer, colon cancer, prostate cancer, ovary cancer, uterocervical cancer, breast cancer, kidney cancer, bladder cancer, brain tumor, etc).

The compounds of the present invention also possess the ability to regulate pancreas function and are thus useful as a pharmaceutical composition, which can be used as an agent for preventing or treating some kinds of pancreatic diseases (e.g., acute or chronic pancreatitis or pancreas cancer, etc.).

The compounds of the present invention also possess a placenta function regulating activity and are thus useful as a pharmaceutical composition, which can be used as an agent for preventing or treating cilia cancer, hydatid moles, invasive moles, miscarriage, fetal hypoplasia, sugar dysbolism, lipid dysbolism or labor induction.

A pharmaceutical composition comprising the compound of the present invention has a low toxicity, and can be formulated, according to means known generally used in production of medicinal preparations, as it is or in admixture with a pharmacologically acceptable carrier, into for example tablets (including sugar-coated tablet and film-coated tablet), powders, granules, capsules (including soft capsule), liquid, injections, suppository, sustained release preparations and the like, and safely administered orally or parenterally (e.g., topical, rectal, intravenous administrations, etc.). The content of the compound of the present invention in the preparation of the present invention is from about 0.01 to about 100 wt % based on the whole preparation. The dose of the compound of the present invention varies depending on subject to be administered, target organs, conditions, routes for administration, etc.; in oral administration, e.g., for a cancer patient, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for a cancer patient, to administer the compound of the present invention intravenously in a daily dose of about 0.01 to about 30 mg, preferably about 0.1 to about 20 mg, and more preferably about 0.1 to about 10 mg (as 60 kg body weight). The dosage can be adjusted to account for the weight of the subject according to methods known in the art.

Pharmacologically acceptable carriers which may be used in production of a preparation of the present invention include various conventional organic or inorganic carrier substances. Preparation materials also include, e.g., an excipient, brightener, binder and disintegrating agent in a solid preparation, and a solvent, solubilizer, suspending agent, isotonization agent, buffer, soothing agent and the like in a liquid preparation. Further, if necessary, usual additives such as a preservative, antioxidant, coloring agent, sweetener, adsorbent, wetting agent and the like can be appropriately used in suitable amounts.

Examples of useful exipients include, but are not limited to, lactose, sucrose, D-mannitol, starch, corn starch, crystalline cellulose, light anhydrous silic acid, etc.

Examples of useful brighteners include, but are not limited to, magnesium stearate, calcium stearate, talc, colloidal silica, etc.

Examples of useful binders include, but are not limited to, crystalline cellulose, sucrose, D-mannitol, dextrin, hydroxypropyl cellulose, hydroxypropylmethyl cellulose, polyvinylpyrrolidone, starch, saccharose, gelatin, methyl cellulose, carboxymethyl cellulose sodium, etc.

Examples of useful disintegrating agents include, but are not limited to, starch, carboxymethyl cellulose, carboxymethyl cellulose calcium, carboxymethyl starch sodium and L-hydroxypropyl cellulose.

Examples of useful solvents include, but are not limited to, injection water, alcohol, propylene glycol, Macrogol, sesame oil, corn oil and olive oil.

Examples of useful dissociation aids include, but are not limited to, polyethylene glycol, propylene glycol, D-mannitol, benzyl benzoate, ethanol, trisaminomethane, cholesterol, triethanolamine, sodium carbonate and sodium citrate.

Examples of useful suspending agents include, but are not limited to, surfactants such as stearyltriethanolamine, sodium laurylsulfate, laurylaminopropionic acid, lecithin, benzalkonium chloride, benzethonium chloride, glycerine monostearate and the like; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose and the like.

Examples of useful isotonization agents include, but are not limited to, glucose, D-sorbitol, sodium chloride, glycerine and D-mannitol.

Examples of useful buffers include, but are not limited to, buffering solutions of a phosphate, acetate, carbonate and citrate.

Examples of useful soothing agents include, but are not limited to, benzyl alcohol, etc.

Examples of useful preservatives include, but are not limited to, p-hydroxybenzoates, chlorobutanol, benzyl alcohol, phenethyl alcohol, dehydroacetic acid and sorbic acid.

Examples of useful antioxidants include, but are not limited to, a sulfite, ascorbic acid and α-tocopherol.

Examples of useful compounds of the present invention can be used simultaneously with drugs other than the compound of the present invention. Examples of the drug which can be used simultaneously with the compound of the present invention (hereinafter referred to as a combination drug) include agents for treating cancer such as chemotherapeutic agents, hormonal therapeutic agents, and immunotherapeutic agents.

Examples of the chemotherapeutic agents include, but are not limited to, alkylating agents, antimetabolites antagonists, anticancer antibiotics, and plant-derived anticancer agents.

Examples of alkylating agents include but are not limited to nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, rnelphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, and bizelesin.

Examples of antimetabolites include, but are not limited to, mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine.

Examples of anticancer antibiotics include, but arc not limited to, actinomycin-D, actinomycin-C, mitomycin-C, chromomycin-A3, bleomycin hydrochloridc, bleomycin sulfate, pcplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, and idarubicin hydrochloride.

Examples of plant-derived anticancer agents include, but are not limited to, etoposide, etoposide phosphate, vinblastine sulfate, vincristine sulfate, vindesine sulfate, teniposide, paclitaxel, docetaxel, and vinorelbine.

Examples of hormonal therapeutic agents include, but are not limited to, fosfestrol, diethylstylbestrol, chlorotrianisene, medtoxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimidc, LH-RH agonists (e.g., goserelin acetate, buserelin, leuprorelin), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide), 5α-reductase inhibitors (e.g., finasteride, episteride), adrenocorticohormone drugs (e.g., dexamethasone, prednisolone, betamethasone, triamcinolone), androgen synthesis inhibitors (e.g., abiraterone), and retinoid and drugs that retard retinoid metabolism (e.g., liarozole). LH-RH agonists (e.g., goserelin acetate, buserelin, leuprorelin) are preferable.

Examples of immunotherapeutic agents (BRM) include, but are not limited to, picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, and procodazole.

The combination of the compounds of the present invention with combination drugs provide the following beneficial effects:

(1) the dose can be reduced in comparison with a case in which the compound of the present invention or a combination drug is administered alone;

(2) a drug to be combined with the compound of the present invention can be selected depending on symptoms (mild, serious and the like) of patients;

(3) the therapeutic period can be lengthened by selecting a combination drug having a different action mechanism than that of the compound of the present invention;

(4) the therapeutic effect can be sustained by selecting a combination drug having a different action mechanism than that of the compound of the present invention; and (5) by combining the compound of the present invention with a combination drug, synergic effect can be obtained.

Hereinafter, combined use of the compound (I) of the present invention with a combination drug is referred to as "combination agent of the present invention".

When using a combination agent of the present invention, the administration time of the compound of the present invention and a combination drug is not restricted, and the compound of the present invention or a pharmaceutical composition thereof and a combination drug or a pharmaceutical composition thereof can be administered to an administration subject simultaneously, or may be administered at different times. The dosage of a combination drug may be determined according to the administration amount clinically used, and can be appropriately selected depending on an administration subject, administration route, disease, combination and the like.

The administration mode of a combination agent of the present invention is not particularly restricted, and it is sufficient that the compound of the present invention and a combination drug are combined in administration. Examples of such administration modes include the following methods: (1) the compound of the present invention and a combination drug are simultaneously produced to give a single preparation which is administered; (2) the compound of the present invention and a combination drug are separately produced to give two kinds of preparations which are administered simultaneously by the same administration route; (3) the compound of the present invention and a combination drug are separately produced to give two kinds of preparations which are administered by the same administration route only at the different times; (4) the compound of the present invention and a combination drug are separately produced to give two kinds of preparations which are administered simultaneously by the different administration routes; and (5) the compound of the present invention and a combination drug are separately produced to give two kinds of preparations which are administered by the different administration routes only at different times (for example, the compound of the present invention and a combination drug are administered in this order, or in the reverse order).

The combination agent of the present invention has low toxicity. Thus, the compound of the present invention and/or the above-mentioned combination drug can be mixed, according to a method known in the art, with a pharmacologically allowable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., local, rectum, vein, and the like). An injection can be administered by intravenous, intramuscular, subcutaneous or intraorgan route, or directly to the lesion.

Any pharmacologically allowable carrier know in the art may be used in production of a combination agent of the pharmaceutical composition of the present invention, e.g., various organic or inorganic carrier substances conventionally used. Examples of other ingredients include an excipient, lubricant, binder and disintegrating agent in a solid preparation, or a solvent, dissolution aid, suspending agent, isotonizing agent, buffer, soothing agent and the like in a liquid preparation. Further, if desirable, usual additives such as a preservative, antioxidant, coloring agent, sweetening agent, adsorbent, wetting agent and the like can also be appropriately used in suitable amount.

Examples of useful excipients include, but are not limited to, lactose, sucrose, D-mannitol, starch, corn starch, crystalline cellulose, light anhydrous silicic acid and the like.

Examples of useful lubricants include, but are not limited to, magnesium stearate, calcium stearate, talc, colloidal silica and the like.

Examples of useful binders include, but are not limited to, crystalline cellulose, sucrose, D-mannitol, dextrin, hydroxypropylcellulose, hydroxypropylmethylcllulose, polyvinylpyrrolidone, starch, sucrose, gelatin, methylcellulose, carboxymethylcellulose sodium and the like.

Examples of useful disintegrating agents include starch, carboxymethylcellulose, carboxymethylcellulose calcium, carboxymethylstarch sodium, L-hydroxypropylcellulose and the like.

Examples of useful solvents include injection water, alcohol, propylene glycol, macrogol, sesame oil, corn oil, olive oil and the like.

Disclosed as examples of the dissolution aid are polyethylene glycol, propylene glycol, D-mannitol, benzyl benzoate, ethanol, trisaminomethane, cholesterol, triethanolamine, sodium carbonate, sodium citrate and the like.

Disclosed as examples of the suspending agent are surfactants such as stearyl triethanolamine, sodium laurylsulfate, laurylaminopropionic acid, lecithine, benzalkonium chloride, benzetonium chloride, glycerin monostearate and the like; hydrophilic polymers such as polyvinyl alcohol, polyvinyl pyrrolidone, carboxymethylcellulose sodium, methylcellulose, hydroxymethylcellulose, hydroxyethylceluluose, hydroxypropylcellulose and the like.

Examples of useful isotonizing agents include, but are not limited to, glucose, D-sorbitol, sodium chloride, glycerin, D-mannitol and the like.

Examples of useful buffers include, but are not limited to, buffer solutions of a phosphate, acetate, carbonate, citrate and the like, etc., are listed.

Examples of useful soothing agents include, but are not limited to, benzyl alcohol and the like.

Examples of the preservative include p-oxybenzoates, chlorobutanol, benzyl alcohol, phenetyl alcohol, dehydroacetic acid, sorbic acid and the like.

Examples of the antioxidant include sulfites, ascorbic acid, α-tocopherol and the like.

The compounding ratio of the compound of the present invention to a combination drug in a combination agent in the present invention can be appropriately selected depending on an administration subject, administration route, diseases and the like.

For example, the content of the compound of the present invention in a combination agent of the present invention differs depending on the form of a preparation, and usually from about 0.01 to 100% by weight, preferably from about 0.1 to 50% by weight, further preferably from about 0.5 to 20% by weight, based on the preparation.

The content of a combination drug in a combination agent of the present invention differs depending on the form of a preparation, and usually from about 0.01 to 100% by weight, preferably from about 0.1 to 50% by weight, further preferably from about 0.5 to 20% by weight, based on the preparation.

The content of additives such as a carrier and the like in a combination agent of the present invention differs depending on the form of a preparation, and usually from about 1 to 99.99% by weight, preferably from about 10 to 90% by weight, based on the preparation.

In the case when the compound of the present invention and a combination drug are separately prepared respectively, the same contents may be adopted.

These preparations can be produced by methods known in the art. For example, the compound of the present invention and a combination drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and molded into an oily injection.

In the case of a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxpropylcellulose and the like), a lubricant (e.g., talc, magnesium stearate, polyethylene glycol 6000 and the like) and the like, for example, can be added to the compound of the present invention or a combination drug, according to a method known per se, and the mixture can be compression-molded, then if desirable, the molder product can be coated by a method known per se for the purpose of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid acrylic acid copolymer, manufactured by Rohm, DE), pigment (e.g., iron oxide red, titanium dioxide, et.) and the like can be used. The preparation for oral administration may be any of a quick release preparation and a sustained release preparation.

For example, in the case of a suppository, the compound of the present invention and a combination drug can be made into an oily or aqueous solid, semisolid or liquid suppository according to methods known in the act. As the oily substrate used in the above-mentioned composition, for example, glycerides of higher fatty acids [e.g., cacao butter, Witebsols (manufactured by Dynamite Novel, DE), etc.], intermediate grade fatty acids [e.g., Myglyols (manufactured by Dynamite Novel, DE), etc.], or vegetable oils (e.g., sesame oil, soy bean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

An example of a sustained release agent includes, but is not limited to, sustained release microcapsules. For obtaining a sustained release microcapsule, methods known in the act can be adopted, and for example, it is preferably molded into a sustained release preparation shown in section (2) below, before administration.

The compound of the present invention is preferably molded into an oral administration preparation such as a solid preparation (e.g., powder, granule, tablet, capsule) and the like, or molded into a rectum administration preparation such as a suppository. Particularly, an oral administration preparation is preferable.

A combination drug can be made into the above-mentioned drug form depending on the kind of the drug.

An injection of the compound of the present invention or a combination drug, and preparation thereof, a sustained release preparation or quick release preparation of the compound of the present invention or a combination drug, and preparation thereof, and a sublingual, buccal or intraoral quick disintegrating agent of the compound of the present invention or a combination drug, and preparation thereof, are described below.

(1) Injection and Preparation Thereof

An injection prepared by dissolving the compound of the present invention or a combination drug into water is preferable. This injection may be allowed to contain a benzoate and/or salicylate.

The injection is obtained by dissolving the compound of the present invention or a combination drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, organic acid salts such as tromethamol and the like, are listed.

The concentration of the compound of the present invention or a combination drug in an injection is from 0.5 to 50 w/v %, preferably from about 3 to 20 w/v %. The concentration of a benzoate salt or/and salicylate salt is from 0.5 to 50 w/v %, preferably from 3 to 20 w/v %.

For preparations of the present invention, additives usually used in preparing injections can be appropriately compounded. For example, stabilizers (ascorbic acid, sodium pyrosulfite, and the like), a surfactant (Polysorbate 80, macrogol and the like), solubilizers (glycerin, ethanol and the like), buffers (phosphoric acid and alkali metal salt thereof, citric acid and alkali metal salt thereof, and the like), isotonizing agents (sodium chloride, potassium chloride, and the like), dispersing agents (hydroxypropylmethylcellulose, dextrin), pH regulators (hydrochloric acid, sodium hydroxide and the like), preservatives (ethyl p-oxybenzoate, benzoic acid and the like), dissolving agents (conc. glycerin, meglumine and the like), dissolution aids (propylene glycol, sucrose and the like), a soothing agent (glucose, benzyl alcohol and the like), and the like, can be added. These additives are generally compounded in a proportion usually used in an injection.

It is advantageous that the pH of the injection is controlled from 2 to 12, preferably from 2.5 to 8.0 by addition of a pH regulator.

An injection is obtained by dissolving the compound of the present invention or a combination drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may advantageously be heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 minutes.

Further, a preparation endowed with an antibacterial property of a solution may also be produced so that it can be used as a preparation, which is divided and administered multiple-times.

(2) Sustained Release Preparation or Quick Release Preparation, and Preparation Thereof A sustained release preparation is preferable which is obtained, if desirable, by coating a nucleus containing the compound of the present invention or a combination drug with a film agent such as a water-insoluble substance, swellable polymer and the like. For example, a sustained release preparation for oral administration of one administration per day type is preferable.

As the water-insoluble substance used in a film agent, there are listed, for example, cellulose ethers such as ethylcellulose, butylcellulose and the like, cellulose esters such as cellulose stearate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacryaltelaminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacryalte copolymers, poly(methacrylic anhydride), glycidyl methacrylate copolymer, particularly, acrylic acid-based polymers such as Eudoragits (Rhom Farma) such as Eudoragit RS-100, RL-100, RS-30D, RL-30D, RL-PO, RS-PO (ethyl acryalte·methyl methacryalte·trimethyl chloride methacryalte·ammoniumethyl copolymer), Eudoragit NE-30D (methyl methacryalte·ethyl acrylate copolymer), and the like, hardened oils such as hardened castor oil (e.g., Lovery wax (Freunt) and the like), waxes such as carnauba wax, fatty acid glycerin ester, paraffin and the like, polyglycerin fatty esters, and the like.

As the swellable polymer, polymers having an acidic dissociating group and showing pH dependent swell are preferable, and polymers manifesting small swelling in acidic regions such as in stomach and large swelling in neutral regions such as in small intestine and large intestine are preferable.

As such a polymer having an acidic dissociating group and showing pH dependent swell, cross-linkable polyacrylic acid copolymers such as, for example, Carbomer 934P, 940, 941, 974P, 980, 1342 and the like, polycarbophil, calcium polycarbophil (last two are manufactured by BF Goodrich), Hibiswako 103, 104, 105, 304 (all are manufactured by Wako Purechemical Co., Ltd.), and the like, are listed.

The film agent used in a sustained release preparation may further contain a hydrophilic substance. As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like are listed.

The content of a water-insoluble substance in the film agent of a sustained release preparation is from about 30 to 90% (w/w), preferably from about 35 to 80% (w/w), further preferably from about 40 to 75% (w/w), the content of a swellable polymer is from about 3 to 30% (w/w), preferably from about 3 to 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drug as exemplified below, then, coating the resulting nucleus with a film agent solution prepared by heat-solvating a water-insoluble substance, swellable polymer and the like or by dissolving or dispersing it in a solvent.

1. Preparation of a Nucleus Containing a Drug

The form of the nucleus containing a drug to be coated with a film agent (hereinafter, sometimes simply referred to as nucleus) is not particularly restricted, and preferably, the nucleus is formed into particles such as a granule or fine particle. When the nucleus is composed of granules or fine particles, the average particle size thereof is preferably from about 150 to 2000 $\mu$m, further preferably, from about 500 to 1400 $\mu$m.

Preparation of the nucleus can be effected by a usual production method. For example, a suitable excipient, binding agent, disintegrating agent, lubricant, stabilizer and the like are mixed into a drug, and the mixture is subjected to a wet extrusion granulating method, fluidized bed granulating method or the like, to prepare a nucleus.

The content of drugs in a nucleus is from about 0.5 to 95% (w/w), preferably from about 5.0 to 80% (w/w), further preferably from about 30 to 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binder, for example, polyvinyl alcohol, hydroxypropyl cellulose, polyethylene glycol, polyvinyl pyrrolidone, Pluronic F68, gum Arabic, gelatin, starch and the like are used. As the disintegrating agent, for example, carboxymethylcelulose calcium (ECG505), crosscarmelose sodium (Ac-Di-Sol), crosslinked polyvinylpyrrolidone (Crosspovidone), lower substitution hydroxypropylcellulose (L-HPC) and the like are used. Among them, hydroxypropylcellulose, polyvinylpyrrolidone, lower substitution hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose, waxes can be used, and the average particle size thereof is preferably from about 100 $\mu$m to 1500 $\mu$m.

For separating a drug and a film agent contained in a nucleus, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl group or carboxyalkyl group are used, more preferably, hydroxypropylmethylcellulose and hydroxypropylcellulose are used. The protective agent may contain, as a stabilizer, acids such as tartaric acid, citric acid, succinic acid, fumaric acid, maleic acid and the like, and lubricants such as talc and the like. When the protective agent is used, the coating amount is from about 1 to 15% (w/w), preferably from about 1 to 10% (w/w), further preferably from about 2 to 8% (w/w), based on the nucleus.

The protective agent can be coated by a usual coating method, and specifically, the protective agent can be coated, for example, by a fluidized bed coating method, pan coating method and the like.

II. Coating of Nucleus with Film Agent

A nucleus obtained in the above-mentioned step I is coated with a film agent solution obtained by heat-solvating the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer and hydrophilic substance in a film agent solution is appropriately selected so that the contents of these components in a coated film are the above-mentioned contents, respectively.

The coating amount of a film agent is from about 1 to 90% (w/w), preferably from about 5 to 50% (w/w), further preferably from about 5 to 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty ester, hardened castor oil, triethyl citrate, cetyl alcohol, stearyl alcohol and the like may also be added as a plasticizer.

After coating with a film agent, if necessary, an antistatic agent such as talc and the like may be mixed.

The quick release preparation may be liquid (solution, suspension, emulsion and the like) or solid (particle, pill, tablet and the like). Oral agents and parenteral agents such as an injection and the like are used, and oral agents are preferable.

The quick release preparation may contain, in addition to an active component drug, also carriers, additives and excipients conventionally used in the production field (hereinafter, sometimes abbreviated as excipient). The preparation excipient used is not particularly restricted providing it is an excipient ordinarily used as a preparation excipient. For example, as the expient for an oral solid preparation, lactose, starch, corn starch, crystalline cellulose (Avicel PH101, manufactured by Asahi Chemical Industry Co., Ltd., and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to 99.4 w/w %, preferably from about 20 to 98.5 w/w %, further preferably from about 30 to 97 w/w %, based on the total amount of the quick release preparation.

The content of a drug in the quick release preparation can be appropriately selected in the range from about 0.5 to 95%, preferably from about 1 to 60% based on the total amount of the quick release preparation.

When the quick release preparation is an oral solid preparation, it usually contains, in addition to the above-mentioned components, also a disintegrating agent. As this disintegrating agent, there are used, for example, carboxymethylcellulose calcium (ECG-505, manufactured by Gotoku Yakuhin), crosscarmelose sodium (for example, Actisol, manufactured by Asahi Chemical Industry Co., Ltd.), crosspovidone (for example, Kollidon CL, manufactured by BASF), lower substitution hydroxypropylcellulose (manufactured by Shin-Etsu Chemical Co., Ltd.), carboxymethylstarch (manufactured by Matsutani Kagaku K. K.), carboxymethylstarch sodium (Exprotab, manufactured by Kimura Sangyo), partially α-nized starch (PCS, manufactured by Asahi Chemical Industry Co., Ltd.), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and compounding amount of a drug used, design of releasing property, and the like, and for example, from about 0.05 to 30 w/w %, preferably from about 0.5 to 15 w/w %, based on the total amount of the quick releasing agent.

When the quick release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxylmethylcellulose, polybinylpyrrolidone, pluran, dextrin and the like), a lubricant (e.g., polyethylene glycol, magnesium stearate, talc, light anhydrous silicic acid (for example, aerosil [Nippon Aerosil]), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a coloring agent (e.g., tar coloring matter, caramel, iron oxide red, titanium oxide, riboflavins), if necessary, an appetizing agent (e.g., sweetening agent, aroma and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The quick releasing reparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a quick release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Pulek), and the like, then, subjecting the mixture to a wet extrusion granulation method, fluidized bed granulation method and the like.

Thus obtained quick releasing preparation and sustained releasing preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation together with preparation excipients and the like. It may also be permissible that they are made into granules or fine particles, and filled in the same capsule to be used as a preparation for oral administration.

(3) Sublinguial, Buccal or Intraoral Quick Disintegrating Agent and Preparation Thereof Sublinguial, buccal or intraoral quick disintegrating agents may be a solid preparation such as tablet and the like, or may be an oral mucosa membrane patch (film).

As the sublinguial, buccal or intraoral quick disintegrating agent, a preparation containing the compound of the present invention or a combination drug and an excipient is preferable. It may contain also auxiliary agents such as a lubricant, isotonizing agent, hydrophilic carrier, water-dispersible polymer, stabilizer and the like. Further, for easy absorption and increase in in vivo use efficiency, β-cyclodextrin or β-cyclodextrin derivatives (e.g., hydroxypropyl-β-cyclodextrin and the like) and the like may also be included.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., fine crystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbofil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublinguial, buccal or intraoral quick disintegrating agent can be produced by mixing the compound of the present invention or a combination drug and an excipient by a method known in the art. Further, if desirable, auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or a combination drug and the above-mentioned water-dispersible polymer (preferably, hydroxypropylcellulose, hydroxypropylmethylcellulose), excipient and the like are dissolved in a solvent such as water and the like, and the resulted solution is cast, to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbofil, carbopol) may also be contained. In the casting, a solution is poured on the non-adhesive surface, spread to uniform thickness (preferably, about 10 to 1000 micron) by an application tool such as a doctor blade and the like , then, the solution is dried to form a film. It may be advantageous that thus formed film is dried at room temperature or under heat, and cut into given area.

As the preferable intraoral quick disintegrating agent, there are listed solid quick scattering dose agents composed of a network body comprising the compound of the present invention or a combination drug, and a water-soluble or water-diffusible carrier which is inert to the compound of the present invention or combination drug, are listed. This network body is obtained by sublimating a solvent from the solid composition constituted from a solution prepared by dissolving the compound of the present invention or a combination drug in a suitable solvent.

It is preferable that the composition of an intraoral quick disintegrating agent contains a matrix forming agent and a secondary component, in addition to the compound of the present invention or a combination drug.

Examples of the matrix forming agent include animal proteins or vegetable proteins such as gelatins, dextrins and, soybean, wheat and psyllium seed protein and the like; rubber substances such as gum Arabic, guar gum, agar, xathane gum and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-asparatic acid, L-glutamic acid, L-hydroxyproline, L-isoleucine, L-leucine, L-phenylalanine and the like, are losted.

One or more of the matrix forming agents can be introduced in a solution or suspension before solidification. Such a matrix forming agent may be present in addition to a surfactant, or may be present while a surfactant is being excluded. The matrix forming agent aids to maintain the compound of the present invention or a combination drug in the solution or suspension in diffused condition, in addition to formation of the matrix.

The composition may contain secondary components such as a preservative, antioxidant, surfactant, thickening agent, coloring agent, pH controlling agent, flavoring agent, sweetening agent, food taste masking agent and the like. As the suitable coloring agent, there are listed red, black and yellow iron oxides, and FD & C dyes such as FD & C Blue 2, FD & C Red 40 and the like manufactured by Elis and Eberald. Examples of the suitable flavoring agent include mint, raspberry, licorice, orange, lemon, grape fruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-containing compounds, adsorbent substances and microcapsulated compounds.

The preparation contains the compound of the present invention or a combination drug in an amount usually from about 0.1 to 50% by weight, preferably from about 0.1 to 30% by weight, and preferable are preparations (such as the above-mentioned sublingual agent, buccal and the like) which can dissolve 90% or more the compound of the present invention or a combination drug (into water) within the time range of about 1 to 60 minutes, preferably of about 1 to 16 minutes, more preferably of about 2 to 5 minutes, and intraoral quick disintegrating preparations which are disintegrated within the range of 1 to 60 seconds, preferably of 1 to 30 seconds, further preferably of 1 to 10 seconds after being placed in an oral cavity.

The content of the above-mentioned exipient in the whole preparation is from about 10 to 99% by weight, preferably from about 30 to 90% by weight. The content of β-cyclodextrin or β-cyclodextrin derivative in the whole preparation is from 0 to about 30% by weight. The content of the lubricant in the whole preparation is from about 0.01 to 10% by weight, preferably from about 1 to 5% by weight. The content of the isotonizing agent in the whole preparation is from about 0.1 to 90% by weight, preferably, from about 10 to 70% by weight. The content of the hydrophilic carrier agent in the whole preparation is from about 0.1 to 50% by weight, preferably, from about 10 to 30% by weight. The content of the water-dispersible polymer in the whole preparation is from about 0.1 to 30% by weight, preferably, from about 10 to 25% by weight. The content of the stabilizer in the whole preparation is from about 0.1 to 10% by weight, preferably, from about 1 to 5% by weight. The above-mentioned preparation may further contain additives such as a coloring agent, sweetening agent, preservative and the like, if necessary.

The dose of the compound of the present invention varies depending on subject to be administered, target organs, conditions, routes for administration, etc.; in oral administration, e.g., for a cancer patient, the dose is normally about 0.1 mg to about 100 mg, preferably about 1.0 to about 50 mg, and more preferably about 1.0 to about 20 mg per day (as 60 kg body weight). In parenteral administration, the single dose varies depending on subject to be administered, target organ, conditions, routes for administration, etc. but it is advantageous, e.g., for a cancer patient, to administer the compound of the D present invention intravenously in a daily dose of about 0.01 to about 30 mg, preferably about 0.1 to about 20 mg, and more preferably about 0.1 to about 10 mg (as 60 kg body weight). The dosage can be adjusted to account for the weight of the subject, according to methods known in the art. Of course, since the dose as described above varies depending on various conditions, amounts smaller than the above-mentioned dosage may sometimes be sufficient. Further, amounts over that range sometimes have to be administered.

The amount of a combination drug can be set at any value unless side effects are problematic. The daily dosage in terms of a combination drug differs depending on the severity, age, sex, body weight, sensitivity difference of the subject, administration period, interval, and nature, pharmacy, kind of the pharmaceutical preparation, kind of effective ingredient, and the like, and is not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once or divided into 4-times a day.

In the administration of a pharmaceutical composition of the present invention, the compound of the present invention may be administered after administration of a combination drug or a combination drug may be administered after administration of the compound of the present invention. Alternatively, they may be administered simultaneously. When administered at a time interval, the interval differs depending on the effective ingredient, drug form and administration method, and for example, when a combination drug is administered first, a method in which the compound of the present invention is administered within a time range of from 1 minute to 3 days, preferably from 10 minutes to 1 day, more preferably from 15 minutes to 1 hour after administration of the combination drug is exemplified.

When the compound of the present invention is administered first, a method in which a combination drug is administered within a time range of from 1 minute to 1 day, preferably from 10 minutes to 6 hours, more preferably from 15 minutes to 1 hour after administration of the compound of the present invention is exemplified.

In a preferable administration method, for example, a combination drug which has been formed into an oral administration preparation is administered orally at a daily dose of about 0.001 to 200 mg/kg, and 15 minutes after, the compound of the present invention which has been formed into a parenteral administration preparation is administered parenterally at a daily dose of about 0.005 to 0.5 mg/kg.

The present invention will be further explained in detail by way of the following Reference Examples, Examples and Experimental Examples, but these examples are mere illustration and do not limit the present invention, and variation may be possible in a range without departing from the scope of the present invention.

In the following Examples, "room temperature" usually denotes about 10° C. to about 35° C. % denotes mol/mol % in the case of a yield, denotes volume % in the case of a solvent used in chromatography, and denotes weight % in other cases. In proton NMR spectrum, protons which can not be confirmed because they are broad, such as OH and NH protons, are not described in data.

Other abbreviations used in this text denote the following meanings.
DMF: N,N-dimethylformamide
BisPy: N,N-bis(2-pyridylmethyl)
TFA: trifluoroacetic acid
Gu-Amb: 4-(guanidinomethyl)benzoyl
Pic: pipecolic acid In the specification, the codes of amino acids, peptides, protection groups, activating groups, others are denoted in accordance with the IUPAC-IUB Commission on Biochemical Nomenclature or by the common codes in the art, examples of which are shown below. For amino acids that may have the optical isomer, L form is presented unless otherwise indicated.
Gly: glycine
Ala: alanine
Val: valine
Leu: leucine
lie: isoleucine
Ser: serene
Thr: threonine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
Cys: cysteine
Nle: norleucine
Orn: ornithine
Asx: asparagine or aspartic acid
Glx: glutamine or glutamic acid
Amb: 4-(aminomethyl) benzoic acid
ATP: adenosine triphosphate The sequence identification numbers (SEQ ID NO:) in the sequence listing of the specification indicates the following sequence. [SEQ ID NO: 1] The amino acid sequence of the human metastin The following Examples illustrate the present invention in more detail, but these do not limit the scope of the present invention.

EXAMPLES

General Procedure for Synthesis of Protected Peptide Resins Protected peptide-resins were manually constructed by Fmoc-based solid-phase peptide synthesis. Pbf was employed for Arg side-chain protection. Fmoc deprotection were achieved by 20% piperidine in DMF (2×1 min, 1×20 min). Fmoc-amino acids were coupled by treatment with 5 equiv of reagents (Fmoc-amino acid, N,N'-diisopropylcarbodiimide (DIPCDI), and HOBt·H$_2$O) to free amino group in DMF for 1.5 h.

Preparation Example 1

BisPy-Amb-Phe-Gly-Leu-Arg-Trp-NH$_2$ (FM052a) (SEQ ID NO: 4)

Trp, Arg(Pbf), Leu, Gly, Phe, Amb residues were successively coupled by general coupling protocol on Fmoc-Rink resin (0.51 mmol/g, 78.4 mg, 0.04 mmol). After 20% piperidine treatment, the N-terminal amino group was modified by treatment of the protected peptide resin with 2-pyridinecarboxaldehyde (32 μL, 0.338 mmol) and NaBH(OAc)$_3$ (112 mg, 0.528 mmol) in DMF—methylene chloride at 25° C. for 2 h. The resin was treated with TFA/thioanisole/m-cresol/1,2-ethanedithiol/H$_2$O (160:10:10:5:10:4, 5 mL) at 0° C. for 2 h. The resin was isolated from the reaction mixture by filtration, washed twice with TFA, and the filtrate and the washing were combined for concentration under reduced pressure. After concentration under reduced pressure, ice-cold Et$_2$O was added. The resulting powder was collected by centrifugation and decantation to separate from supernatant, and the powder was washed three times with Et$_2$O, dissolved in 1N acetic acid, and diluted with distilled water. After purification by preparative HPLC (Cosmosil 5C18 AR-II column, Nacalai Tesque: acetonitrile:water), single peak polypeptide was obtained and freeze dried. The purity of the peptide was determined by HPLC. The title cyclic peptide FM052a was thus obtained as tetra-TFA salt (8.43 mg, 15% yield) of colorless freeze-dried powder.

Preparation Example 2

Gu-Amb-Phe-Gly-Leu-Arg-Trp-NH$_2$ (FM053a) (SEQ ID NO: 3)

By use of the essentially similar procedure with that described for the preparation of FM052a except pyridine-2-aldehyde and hydrogenated triacetoxyboron sodium, synthesis of FM053a was carried out. Modification of the N-terminal amino group was performed by treatment with 1H-pyrazole-1-carboxamidine-hydrochloride (29 mg, 0.200 mmol) and N,N-diisopropylethylamine (70 mL, 0.400 mmol) in DMF to give the title peptide FM053a as di-TFA salt (5.96 mg, 14% yield) of colorless freeze-dried powder. Abbreviations: Pbf=2,2,4,6,7-pentamethyldihydrobenzofuran-5-sulfonyl; DMF=N,N-dimethylformamide; BisPy=N,N-bis(2-pyridylmethyl); TFA=trifluoroacetic acid; Gu-Amb=4-(guanidinomethyl)benzoyl;

Experimental Example

Effects of Metastin Derivatives, FM052a and FM053a on Migration of Pancreatic Cancer Ceus (i) Cell Culture Pancreatic cancer cell lines AsPC-1, BxPC-3, Capan-2, CFPAC-1, Panc-1 and Suit-2 were purchased from the American Type Culture Collection. Cells were cultured as monolayers in the appropriate medium supplemented with 10% fetal bovine serum, 100 units/ml penicillin, and 100 μg/ml streptomycin at 37° C., in a humid atmosphere of 5%CO$_2$/95% air. As for AsPC-1 and Panc-1, upon reaching 80% confluence, the medium was removed, the cells were washed in phosphate-buffered saline (PBS) and treated with increasing doses of metastin (Takeda Chemical Industries, Osaka, Japan) with 10% fetal bovine serum and protein was isolated 15 minutes later as described below.

(ii) Patients and Tumor Samples

Thirty patients with pancreatic ductal adenocarcinoma, who had undergone pancreatectomy at our Department between January 1998 and June 2001 were included in this study. Patients with other pancreatic malignancies, such as intraductal papillary mucinbus adenocarcinoma, acinar cell carcinoma and endocrine tumor, were excluded. Histopathologic diagnosis was confirmed by the Department of Pathology of Kyoto University Hospital. Pancreatic cancer was staged according to the pTNM (UICC) system (Sobin, L. H. and Fleming, I. D. *TNM Classification of Malignant Tumors*, fifth edition (1997). Union Internationale Contre le Cancer and the American Joint Committee on Cancer, Cancer. 80: 1803–4., 1997). Tumor specimens were collected after obtaining the patients informed consent in accordance with the institutional guidelines. Samples for mRNA expression were immediately frozen in liquid nitrogen at the time of surgery and stored at −80° C.

(iii) Quantitative RT-PCR

To monitor gene expression, quantitative real-time RT-PCR analysis was done. This approach made use of the 5' exonuclease activity of the DNA polymerase (AmpliTaq Gold) (Bieche, I. et al., *Cancer Res.* 59: 2759–65., 1999; Schmittgen, T. D. et al., *Anal Biochem*. 285: 194–204., 2000; and Yuan, A. et al., Lab Invest. 80: 1671–80., 2000).

Briefly, within the amplicon defined by a gene-specific PCR primer pair, an oligonucleotide probe labeled with two fluorescent dyes was created and designated as TaqMan probe. As long as the probe was intact, the emission of the reporter dye (6-carboxy-fluorescein, FAM) at the 5' end was quenched by the second fluorescence dye (6-carboxy-tetramethyl-rhodamine, TAMRA) at the 3' end. During the extension phase of PCR, the polymerase cleaved the Taq-Man probe, resulting in a release of the reporter dye. The increasing amount of reporter dye emission was detected by an automated sequence detector combined with analysis software (ABI Prism 7700 Sequence Detection System; PE Applied Biosystems). The conditions of the reaction were according to the manufacturer's protocol. 5 μl of CDNA (reverse transcription mixture) with 25 μl TaqMan Universal PCR Master Mix (PE Applied Biosystems) and oligonucleotides at a final concentration of 0.3 μM for primers and 0.2 μM for the TaqMan hybridization probe were analyzed in a 50 μl volume.

The following primers and TaqMan probes were used for analysis (TAKEDA). upstream primer 5'-ACTCACTGGTTTCTTGGCAGC-3' (SEQ ID NO: 5) downstream primer 5'-ACCTTTTCTAATGGCTCCCCA-3' (SEQ ID NO: 6) TaqMan probe 5'(FAM)-ACTGCTTTCCTCTGTGCCACCCACT-(TAMRA)3' (SEQ ID NO: 7) for KiSS-1, and upstream primer 5'-CGACTTCATGTGCAAGTTCGTC-3' (SEQ ID NO: 8) downstream primer 5'-CACACTCATGGCGGTCAGAG-3' (SEQ ID NO: 9) TagMan probe 5' (FAM)-ACTACATCCAGCAGGTCTCGGTGCAGG-(TAMRA)3' (SEQ ID NO: 10) for hOT7T175.

The thermal cycler parameters were 95° C. for 10 min (for heat activation of Taq-Polymerase), followed by 40 cycles of 95° C. for 15 sec and 60° C. for 1 min. Assessment of GAPDH RNA for quality and normalization was done with the TaqMan GAPDH Control Reagent kit (PE Applied Biosystems), which utilizes standard TaqMan probe chemistry.

(iv) Protein Extraction and Western Blotting

Cells were collected into microtubes with a cell scraper and lysed for 60 min in phosphorylation-inhibitory RIPA buffer containing 50 mM HEPES (pH 7.0), 250 mM NaCl, 0.1% Nonidet P-40, 1 mM phenylmethylsulfonyl fluoride (PMSF) and 20 µg/ml gabexate mesilate, then the lysate was sonicated for 10 sec. Total extracts were cleaned by centrifugation at 12,000 rpm for 10 min at 4° C., the supernatants were collected. Protein concentrations were measured using a protein assay kit (Tonein-TP, Otsuka Pharmaceutical, Tokyo, Japan). The lysates were resuspended in one volume of the gel loading buffer which contained 50 mM Tris-HCl (pH 6.7), 4% SDS, 0.02% bromophenol blue, 20% glycerol and 4% 2-mercaptoethanol, and then boiled at 95° C. for 90 sec. The extracted protein was subjected to Western blotting, as previously described (Wada, M. et al., Pancreas. 15: 176–82., 1997). In brief, 30 µg aliquots of protein was size-fractionated to a single dimension by SDS-PAGE (12% gels) and transblotted to a 0.45-µm polyvinylidene difluoride membrane (Bio-Rad, Richmond, Calif.) in a semidry electroblot apparatus (Bio-Rad, Richmond, Calif.). The blots were, then washed three times with TBST buffer and incubated for two hours at RT in the first antibody solution containing anti-phosphoERK antibody (#pTEpY, Promega, Madison, Wis.), anti-phosphop38 MAPK (#pTGpY, Promega, Madison, Wis.) or anti-phosphoJNK(#pTPpY, Promega, Madison, Wis.), 0.2% I-block (Promega, Madison, Wis.). After three washings in TBST buffer, the blots were incubated for one hour at RT with horseradish peroxidase conjugated anti-rabbit IgG at a 1:2000 dilution with TBST buffer. After three washings in TBST buffer, membranes were treated with enhanced chemiluminescence reagents (Amersham Life Sciences, Amersham, UK) according to the manufacturer's protocol. Membranes were exposed to X-ray film for 5–60 seconds. Protein expression was measured by ATTO densito-analyzer system AE-6920M (ATTO Corporation, Tokyo Japan) and the quantity was expressed numerically. The quantity of the target protein was divided by that of beta actin and relative intensities were obtained.

(v) Cell Proliferation Assay

For assaying proliferation, AsPC-1 and Panc-1 cells ($1 \times 10^4$ cells/3 cm diameter dish) were seeded in 10% FBS medium and incubated with increasing doses of metastin for 48 and 96 hours. Cells were trypsinized and cell numbers were counted using hematocytometer.

(vi) Cell Migration and Matrigel Invasion Assays

A polyvinylpyrrolidone-free polycarbonate framed filter (8 µm pores) was set in a microchemotasis chamber (Corning Coster Corp., Cambridge, Mass.). Cells ($2 \times 10^6$ cells in 200 µl RPMI1640 for AsPC-1 and in 200 µl DMEM for Panc-1) and peptide were added to the upper chamber and incubated at 37° C. for 12 hours to allow migration to the lower chamber, which contained 10%FBS/RPMI1640 for AsPC-1 or 5%FBS/DMEM for Panc-1 as a chemoattractant. After removing nonmigrating cells with a cotton swab from the upper surface of the membrane, cells on the lower surface were fixed, stained with Diff-Quick (International Reagent, Kobe, Japan). For quantification, cells were counted under a microscope in five predetermined fields at X(200.

Cells and peptide ($2 \times 10^6$ cells in 200 µl RPMI1640 for AsPC-1 and in 200 µl DMEM for Panc-1) were added to a Matrigel-coated Transwell(8 µm pores, Becton Dickinson Labware, Bedford, Mass.) and incubated at 37° C. for 12 hours versus a lower chamber containing 10%FBS/RPMI1640 for AsPC-1 or 5%FBS/DMEM for Panc-1. After removing the Matrigel and cells from the upper surface of the membrane, cells on the lower surface were fixed, stained. with Diff-Quick and quantified the number as well. Invasion index was defined as the number of invasion cells per that of migrating cells.

(vii) Statistical Analyses

The comparative statistical evaluations among groups in the densitometry or in the migratory activity were first performed by a two-way analysis of variance (ANOVA) for repeated measures, followed by a post-hoc test using a Turkey Kramer HDS. To compare the mRNA levels in pancreas tissues, Wilcoxon rank sum test was performed. Clinicopathologic characteristics were compared in 30 patients with high and low KiSS-1 or hOT7T175 using the chi-squared test (or Fisher's exact probability test). All assays were performed three times independently. Statistical analyses were done using JMP statistical software (version 3.02) for Macintosh. Probability p value of <0.05 was considered statistically significant.

(viii) KiSS-1 and hOT7T175 Expression in Pancreatic Cancer Tissue

First, the mRNA levels of KiSS1 and its receptor hOT7T175 in 30 invasive ductal carcinoma and in five adjacent normal pancreas were investigated by real time RT-PCR (FIG. 1). Low levels of metastin mRNA were detected in 5/5 normal pancreas tissues while only 14/30 of pancreatic ductal carcinoma tissues expressed metastin. Pancreatic cancer tissues tended to express lower metastin mRNA than normal pancreatic tissues. In contrast, the expression of metastin receptor hOT7T175 mRNA was detected in 30/30 pancreatic cancer although nearly no expression was observed in normal pancreatic tissues.

Statistically, pancreatic cancer tissues were likely to express less metastin than normal pancreatic tissue (p=0.0183) and likely to express higher metastin receptor hOT7T175 than normal pancreatic tissues (p=0.0272). In paired five samples, hOT7T175 expression was overexpressed in all pancreatic cancers compared with adjacent normal pancreatic tissue specimens (data not shown). No apparent correlation was found between levels of metastin and hOT7T175 expression and clinicopathological factors such as tumor size, TNM state, retroperitoneal invasion or neural invasion.

(ix) Expression of Metastin and its Receptor in Pancreatic Cancer Cell Lines

Figure 2:
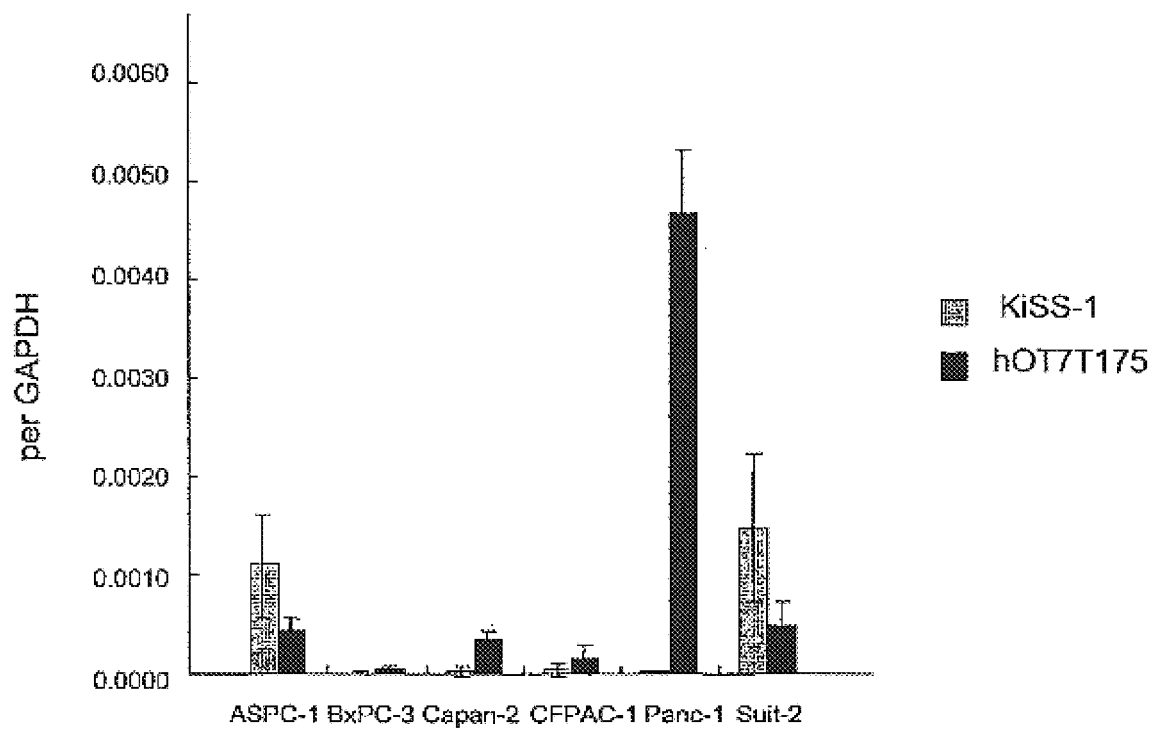
FIG. 2 shows KiSS-1 mRNA and hOT7T175 mRNA expression in six pancreatic cancer cell lines.

Expression of metastin mRNA and its receptor hOT7T175 mRNA in six pancreatic cancer cell lines were measured by real time RT-PCR (FIG. 2) as described above. In six pancreatic cancer cells, AsPC-l and Suit-2 expressed low levels of metastin while other four cell lines did not. In contrast, all cell lines expressed hOT7T175, a receptor of human metastin, and Panc-1 expressed it most strongly. According to these results, AsPC-1 cell line was selected as a representative of low expression of hOT7T175 and Panc-1 cell line was selected as that for high hOT7T175 expression, and AsPC-1 and Panc-1 were used in the following study.

Figure 3:
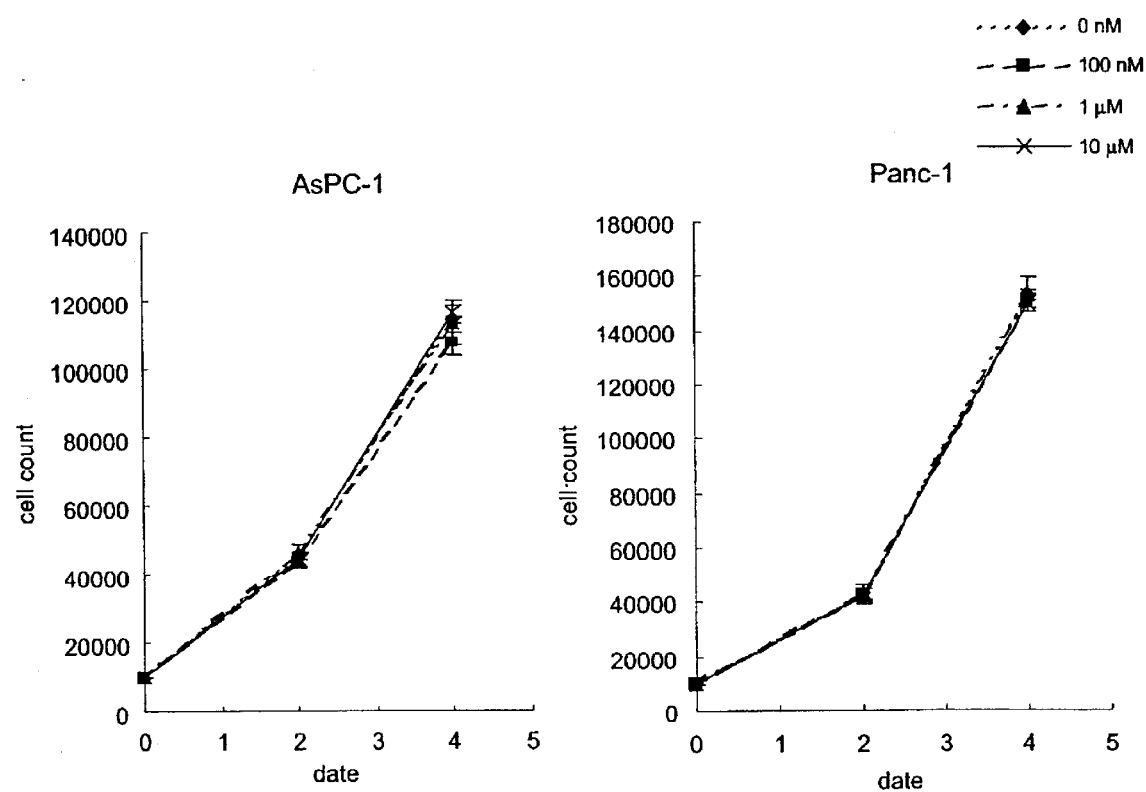
FIG. 3 shows influence of metastin on pancreatic cancer cell growth (AsPC-1 and Panc-1). Bars are Mean±SD.

(x) Influence of Endogenous Metastin Receptor on Proliferation, Migration and Invasiveness Proliferating effect of metastin on pancreatic cancer was examined using above two cell lines. Recombinant metastin was added to AsPC-1 cells and Panc-1 cells in the phase of exponential growth at a final concentration of 0, 100 nM, 1 $\mu$M and 10 $\mu$M for 48 hours and 96 hours. FIG. 3 shows cell growth curve of AsPC-1 cells or Panc-1 cells under incubation of metastin. Neither AsPC-1 nor Panc-1 showed growth retardation with metastin incubation, which suggests no influence of metastin on pancreatic cancer cell growth.

Figure 4:
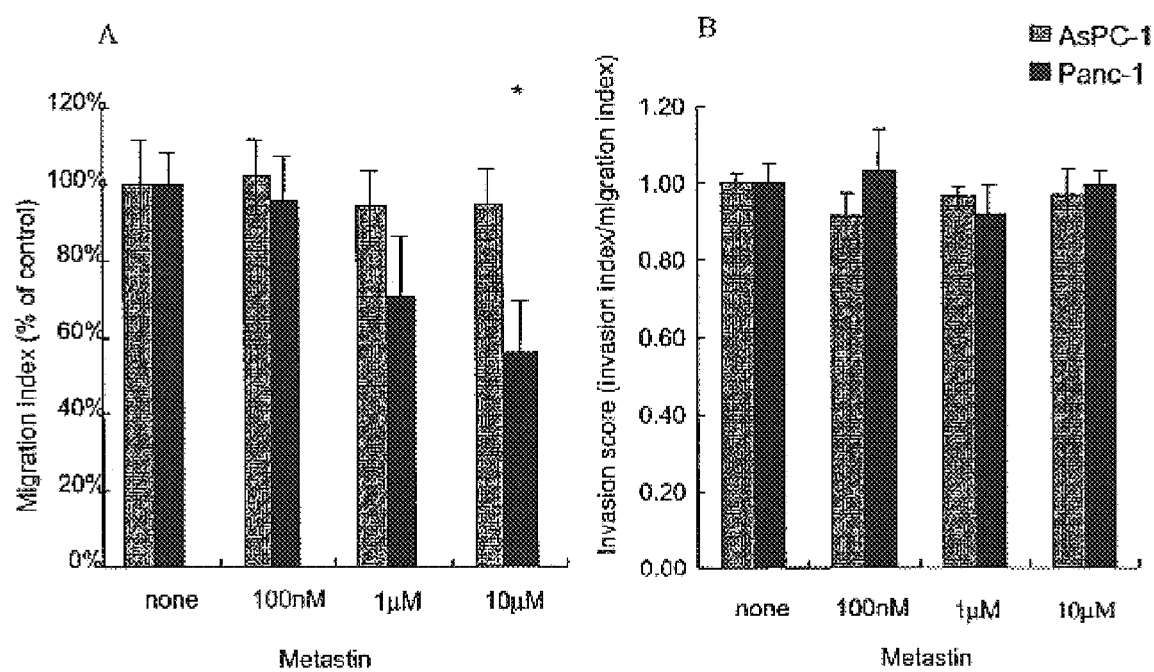
FIG. 4A shows migration assay of AsPC-1 and Panc-1 with indicated concentrations of metastin for 12 hours. Bars are Mean±SD. * represents p<0.01 against.
FIG. 4B shows invasion assay of AsPC-1 and Panc-1 cells with metastin for 12 hours. Bars are Mean±SD. * represents p<0.01 against control.

Next, the influence of metastin on migratory activity and on invasive activity in these cell lines were investigated. FIG. 4A shows the migration score of AsPC-1 and Panc-1 under increasing doses of metastin (0 nM, 100 nM, 1 $\mu$M, 10 $\mu$M) for 12 hours. $2 \times 10^6$/ml cells were incubated with metastin in the upper chamber to allow migration to the lower chamber, which contained 10%FBS/medium as a chemoattractant. Metastin suppressed migratory activity of Panc-1 cells up to 40% reduction ($p<0.01$), while that of AsPC-1 was shown to be little influenced. Migration score of Panc-1 is also significantly reduced compared to AsPC-1 in 1 and 10 $\mu$M attachment of metastin ($p<0.01$, both), although slightly reduced migration of AsPC-1 cells was observed. In contrast, neither cell lines showed any reduction of invasiveness with concomitant incubation of metastin, when compensated by migration activity (FIG. 4B). FIG. 4b shows invasion assay of AsPC-1 and Panc-1 cells with metastin for 12 hours. Cells and peptide ($2 \times 10^6$ cells /ml) were added to a Matrigel-coated Transwell and incubated at 37° C. for 12 hours versus a lower chamber containing 10%FBS/medium. Invasion activity was not influenced both in AsPC-1 and in Panc-1 with attachment of 10 $\mu$M metastin.

(xi) ERK Activation through Endogenous Metastin Receptor

Figure 5A:
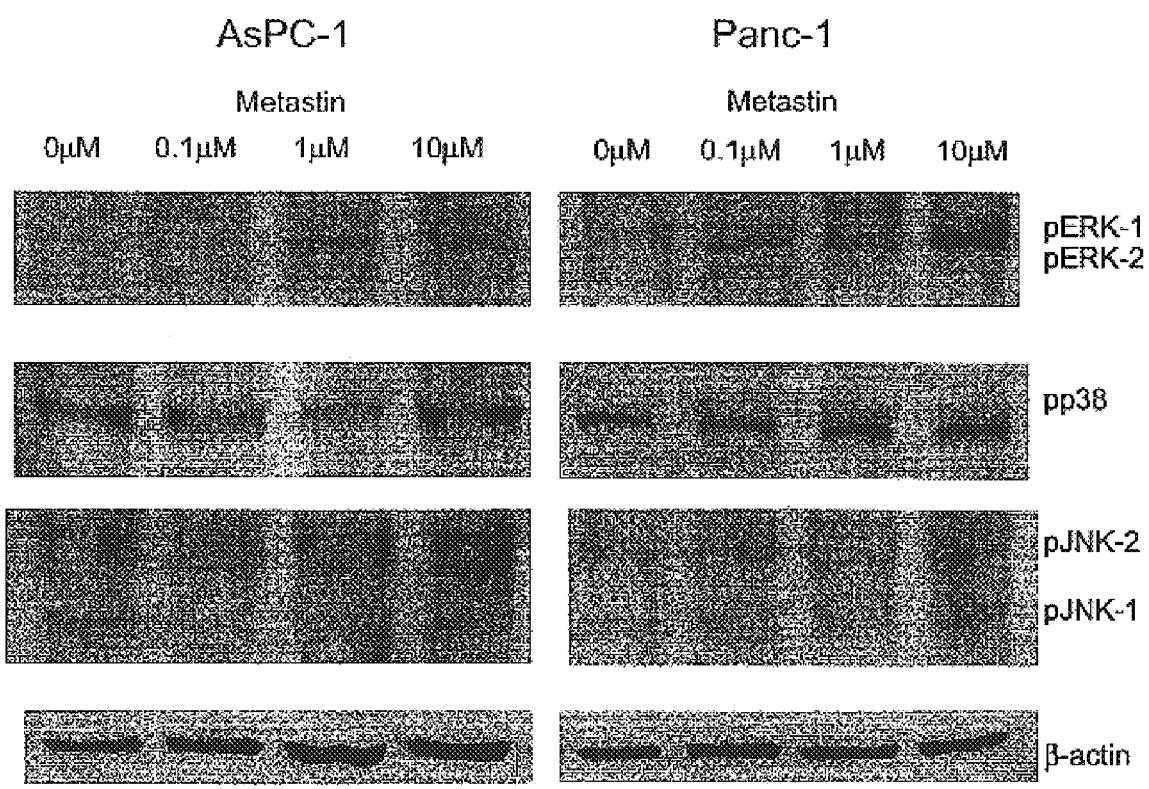
FIG. 5A shows Western blot analysis of MAPK activation of AsPC-1 cells and of Panc-1 cells after treatment with metastin.
Figure 5B:
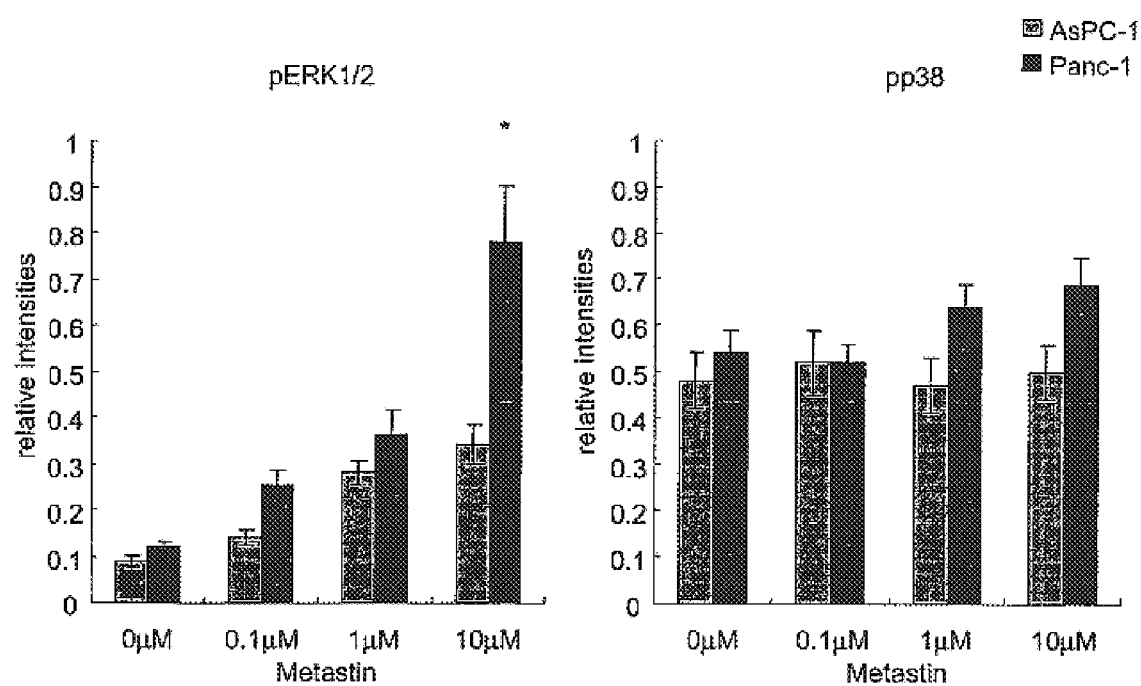
FIG. 5B shows relative intensities of pERK1/2 and of pp38 in AsPC-1 and in Panc-1 cells after treatment with metastin. Results are representative of three independent experiments. Bars are Mean±SD. * represents p<0.01 against AsPC-1.

To evaluate the signaling pathways activated by endogenous metastin receptors in pancreatic cancer, activation of MAPK was examined by treatment with metastin. Cells in exponential stage were incubated in serum containing medium and then transferred to the 1% BSA medium with metastin, as in the case of migration or invasion assay. After incubation with increasing dose of metastin (0 $\mu$M, 0.1 $\mu$M, 1 $\mu$M, 10 $\mu$M) for 15 minutes, activation of ERK1/2, p38 and JNK/1/2 were measured by immunoblot (FIG. 5A). Western blot analysis identified double band corresponding to phosphorylated ERK1 (pERK 1) and pliosphorylated ERK2 (pERK2), single band of phosphorylated, p38 (pp38), and double band showing phosphorylated JNK1 (pJNK1) and phosphorylated JNK2 (pJNK2). pERK1 was augmented as the doses of attached metastin increased both in AsPC-1 and in Panc-1. Slight activation of p38 was observed in Panc-1 while not in the AsPC-1. There was no reduction or increase of pJNKs with attachment of metastin. FIG. 5B shows relative intensities of pERK/1/2 and of pp38 in AsPC-1 and in Panc-1 cells. Metastin increased activation of ERK1 both in Panc-1 and in AsPC-1 and slightly activated p38 but not JNK in Panc-1 in a dose dependent manner in these conditions (FIG. 5B).

Figure 7A:
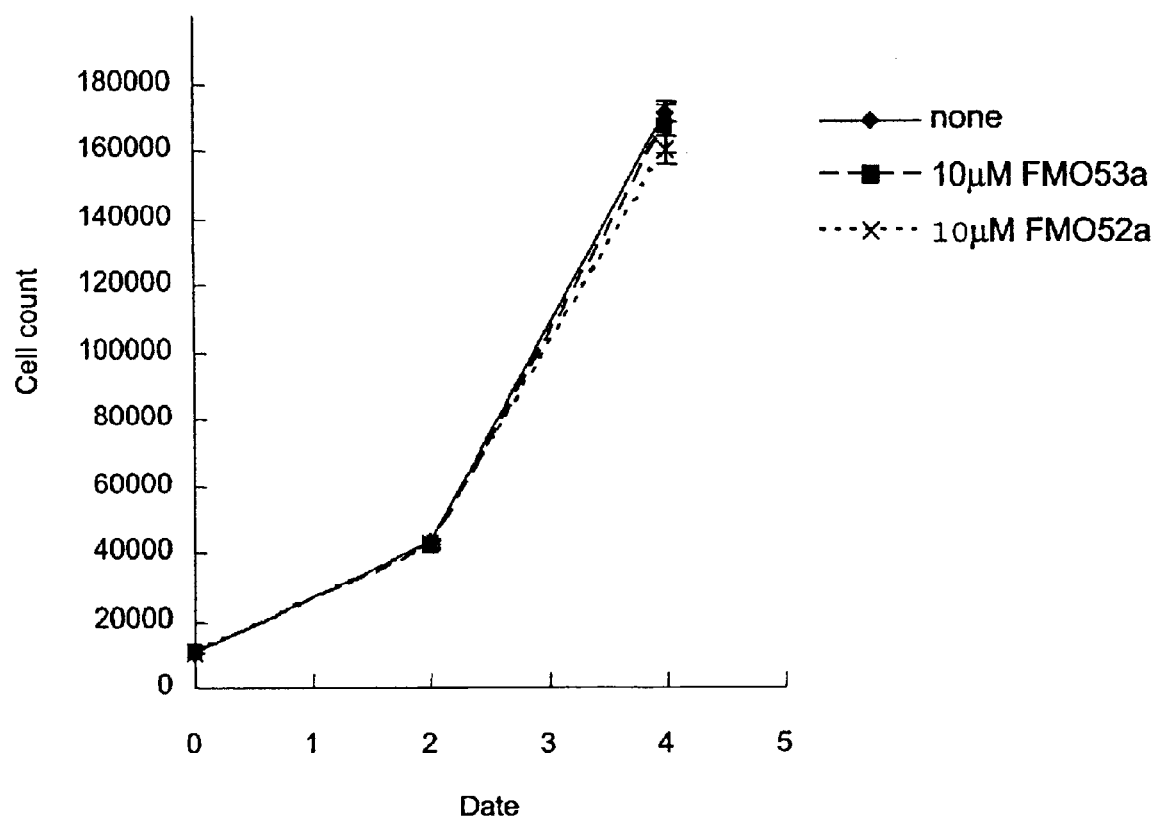
FIG. 7A shows proliferation assay of Panc-1 with KiSS-1 short derivatives.
Figure 7B:
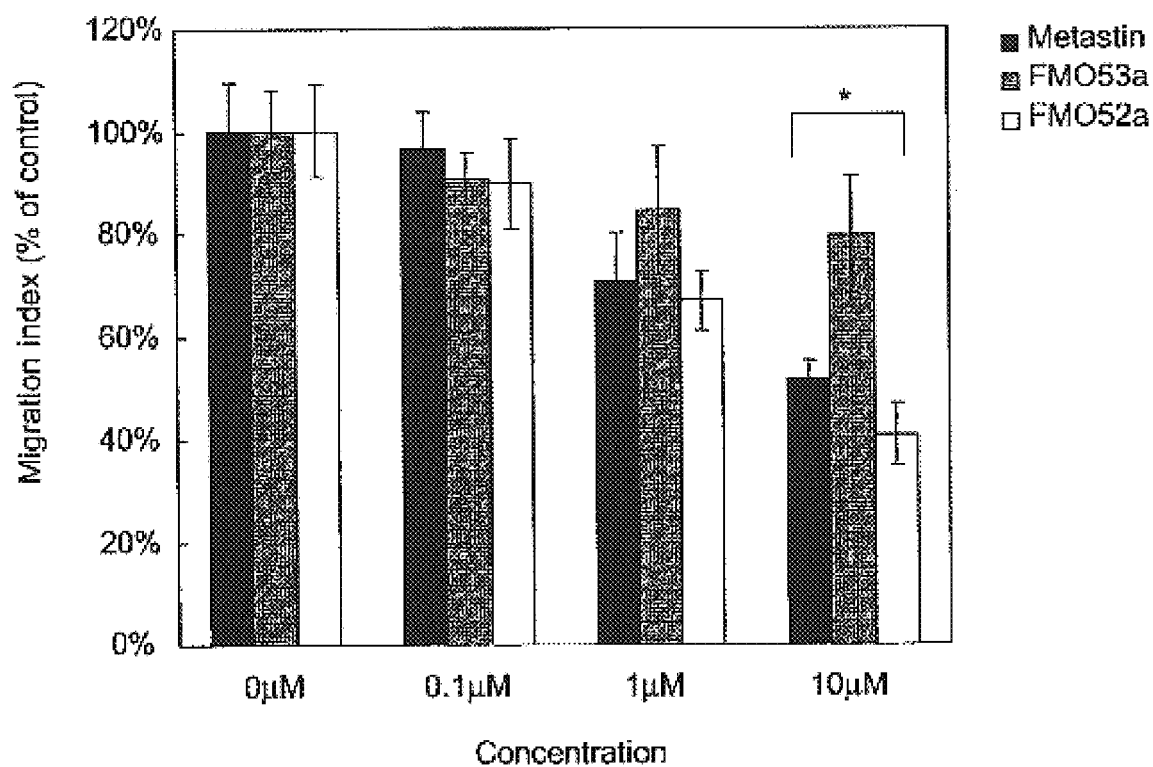
FIG. 7B shows migration assay of Panc-1 with these derivatives. Bars are Mean±SD. * represents p<0.05 against control.
Figure 7C:
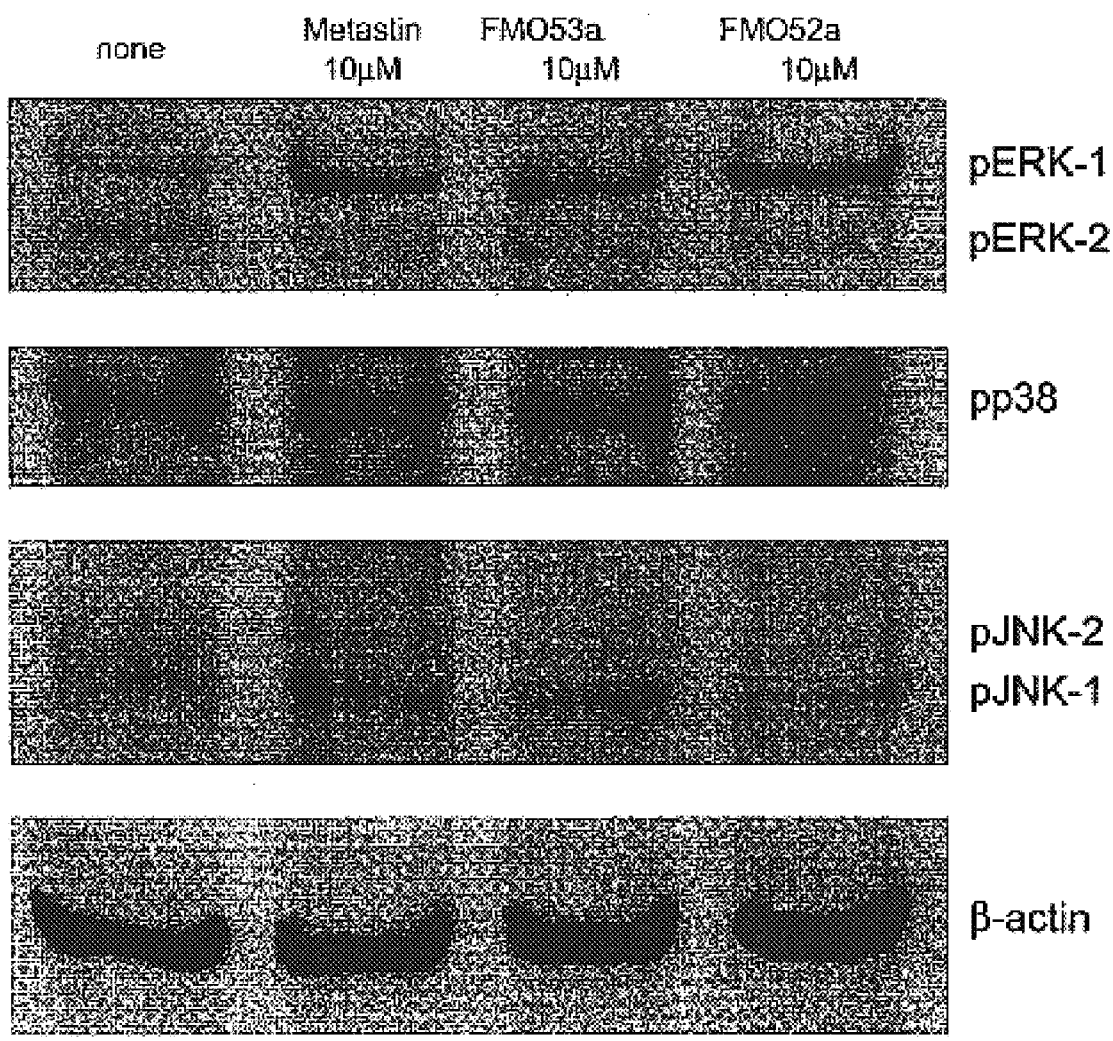
FIG. 7C shows MAPK activation with attachment of two derivatives.

(xii) KiSS-1 Derived Peptides, FM053a and FM052a, Reduced Migration of hOT7T175 Expressing Cancer Cell Line Two shorter variants of metastin-52 peptide were synthesized as described above and were defined as FM053a and FM052a, respectively (FIG. 6). Potential dibasic cleavage sites (RK/RR) and cleavage/amidation sites (GKR) are indicated by bold letters. Underlined letters show predicted signal peptide. Their biological activities on Panc-1 cells which strongly expresses hOT7T175 were examined. FIG. 7A shows the proliferation activity of Panc-1 with incubation of two peptides, KiSS-1 short derivatives, FM053a and FM052a. As expected, cell growth was not affected by these two derivatives. In migratory activity assay, these two peptides reduced the migration index of Panc-1 cells although FM053a is less suppressive than FM052a which possesses the nearly same activity with metastin. (FIG. 7B). To compare the signal transduction of these peptides with metastin, the activation of ERK1/2, p38 and JNK was examined by immunoblot as descried above. ERK1 activation was observed in the Panc-1 cells with attachment of these two peptides as well as metastin. However, Panc-1 cells with FM053a attachment showed less activation of pERK1 than FM052a which well agreed with the previous migration inhibitory result. pp38 was slightly activated after incubation with the two derivatives and pJNKs was not augmented (FIG. 7C). The ERK activation rates seemed to be quite correlative with the migration-suppressive degrees of these peptide.

INDUSTRIAL APPLICABILITY

The metastin derivative (I) of the present invention or a salt thereof or a pro-drug thereof has the excellent cancer metastatis suppressing activity and cancer proliferation suppressing activity, and is useful as a drug for preventing or treating cancers (e.g. lung cancer, stomach cancer liver cancer, pancreas cancer, large intestine cancer, rectum cancer, colon cancer, prostate cancer, ovary cancer, cervix uteri cancer, breast cancer, kidney cancer, bladder cancer, ovary cancer, cervix uteri cancer, breast cancer, kidney cancer, bladder cancer, brain tumor, etc.). The metastin derivative of the present invention or a salt thereof or a pro-drug thereof has a pancreas function regulating activity, and is useful as a drug for preventing or treating pancreatic disease (e.g. acute or chronic pancreatitis, pancreas cancer etc.). The metastin derivative of the present invention or a salt thereof or a pro-drug thereof has a placenta function regulating activity, and is useful as a drug for preventing or treating villus cancer, hydatidiform mole, invasive mole, miscarriage, ateliosis of fetus, sugar dysbolism, fat dysbolism or delivery inducement.

We claim:

1. A metastin derivative represented by the formula:

X-AA$_1$-AA$_2$-AA$_3$-AA$_4$-Z   (I)

wherein X is a group represented by the formula:

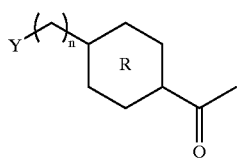

wherein Y is a group represented by the formula:

(i)

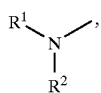   (Y$^1$)

(ii)

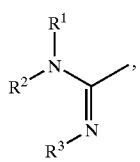   (Y$^2$)

(iii)

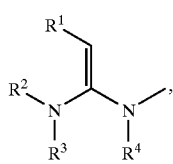   (Y$^3$)

(iv)

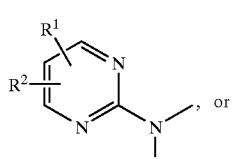   (Y$^4$)

(v)

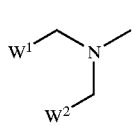   (Y$^5$)

wherein R$^1$, R$^2$, R$^3$ and R$^4$ are each selected from a hydrogen atom or a C$_{1-6}$ alkyl group, W$^1$ and W$^2$ are each selected from a hydrogen atom, a C$_{1-6}$alkyl group, a C$_{6-14}$ aryl group or a heterocyclic group, R is a group represented by the formula:

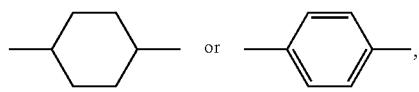

n is 0,1 or 2,

AA$_1$ is a natural or unnatural aromatic amino acid,
AA$_2$ is Gly, Ala, Pro or Pic,
AA$_3$ is an aliphatic amino acid,
AA$_4$ is a basic amino acid or citrulline,
and Z is selected from:
(i) a natural or unnatural aromatic amino acid, or an amide thereof, or an ester thereof,
(ii) a group represented by the formula:

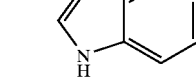   (Wa)

wherein n$_1$ is 0, 1 or 2,
(iii) a group represented by the formula:

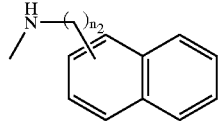   (Wb)

wherein n$_2$ is 0, 1 or 2, or
(iv) a group represented by the formula:

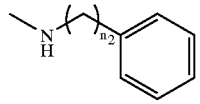   (Wc)

wherein n$_2$ is 0,1 or 2, or a salt thereof.

2. A metastin derivative (I) as claimed in claim 1 selected from 4-[N,N-Bis(2-pyridylmethyl)aminomethyl]benzoyl-Phe-Gly-Leu-Arg-Trp-NH$_2$ (FM052a)(SEQ ID NO: 4), 4-(guanidinomethyl)benzoyl-Phe-Gly-Leu-Arg-Trp-NH$_2$ (FM053a)(SEQ ID NO: 3) or a salt thereof.

3. A pro-drug of a metastin derivative (I) as claimed in claim 1 or a salt thereof.

4. A pharmaceutical composition comprising a pharmaceutically acceptable carrier and a therapeutically effective amount of a metastin derivative (I) as claimed in claim 1, or a salt thereof or a pro-drug thereof.

5. The pharmaceutical composition as claimed in claim 4 which is an agent for suppressing cancer metastasis or an agent for suppressing cancer proliferation.

6. The pharmaceutical composition as claimed in claim 4 which is an agent for preventing or treating cancer.

7. A method for suppressing cancer metastasis or suppressing cancer proliferation in a mammal which comprises administering to the mammal an effective amount of a metastin derivative (I) as claimed in claim 1, or a salt thereof or a pro-drug thereof.

8. A method for preventing or treating cancer in a mammal which comprises administering to the mammal an effective amount of a metastin derivative (I) as claimed in claim 1, or a salt thereof or a pro-drug thereof.

9. An agent for suppressing cancer metastasis or suppressing cancer proliferation comprising a metastin derivative (I) as claimed in claim 1, or a salt thereof or a pro-drug thereof.

10. An agent for preventing or treating cancer proliferation comprising a metastin derivative (I) as claimed in claim 1, or a salt thereof or a pro-drug thereof.

* * * * *